United States Patent [19]
Bowen et al.

[11] Patent Number: 6,072,050
[45] Date of Patent: Jun. 6, 2000

[54] SYNTHETIC PROMOTERS

[75] Inventors: Benjamin A. Bowen, Des Moines; Wesley B. Bruce; Guihua Lu, both of Urbandale; Lynne E. Sims, Polk; Laura A. Tagliani, Akeny, all of Iowa

[73] Assignee: Pioneer Hi-Bred International, Inc., Des Moines, Iowa

[21] Appl. No.: 09/028,819

[22] Filed: Feb. 24, 1998

Related U.S. Application Data

[63] Continuation-in-part of application No. 08/661,601, Jun. 11, 1996, abandoned.

[51] Int. Cl.[7] .............................. A01H 5/00; A01H 4/00; C12N 15/00; C12N 15/29; C12N 15/82
[52] U.S. Cl. .............. 536/24.1; 536/23.6; 536/24.2; 800/278; 800/295; 800/298; 435/419; 435/468; 435/172.3
[58] Field of Search .................. 536/24.1, 23.6, 536/24.2; 435/419, 468, 172.3; 800/278, 298, 295

[56] References Cited

U.S. PATENT DOCUMENTS

| | | | |
|---|---|---|---|
| 5,097,025 | 3/1992 | Benfey et al. | 536/27 |
| 5,106,739 | 4/1992 | Comai et al. | 435/172.3 |
| 5,290,924 | 3/1994 | Last et al. | 536/24.1 |
| 5,322,938 | 6/1994 | McPherson et al. | 536/24.1 |
| 5,510,474 | 4/1996 | Quail et al. | 536/24.1 |
| 5,573,932 | 11/1996 | Ellis et al. | 435/172.3 |

FOREIGN PATENT DOCUMENTS

| | | | |
|---|---|---|---|
| 0 278 659 A2 | 2/1988 | European Pat. Off. | C12N 15/00 |
| 0 342 926 A2 | 5/1989 | European Pat. Off. | C12N 15/00 |
| 0 342 926 | 11/1989 | European Pat. Off. | |
| 0 459 643 A2 | 5/1991 | European Pat. Off. | C12N 15/82 |
| WO 92/14824 | 9/1992 | WIPO | |
| WO 94/01571 | 1/1994 | WIPO | C12N 15/82 |
| WO 95/14098 | 5/1995 | WIPO | C12N 15/82 |
| WO 97/47756 | 12/1997 | WIPO | C12N 15/82 |

OTHER PUBLICATIONS

Odell et al., Identification of DNA sequences required for activity of the cauliflower mosaic virus 35S promotor, Nature, vol. 313:810–812 (1985) XP002915192.

International Search Report mailed Aug. 8, 1999.

Cornejo et al., "Activity of a Maize Ubiquitin Promoter in Transgenic Rice," Plant Molecular Biology, vol. 23, (1993), pp. 567–581.

*Primary Examiner*—Lynette R. F. Smith
*Assistant Examiner*—Thomas Haas
*Attorney, Agent, or Firm*—Alston & Bird LLP

[57] ABSTRACT

Synthetic elements for enhancing expression of genes in plant cells are disclosed. These include a promoter with a "TATA to start" sequence containing 64% or greater GC content and an synthetic upstream element incorporating several OCS binding motifs and novel flanking sequences. Upstream activating regions (UARs) are also disclosed that can further increase the constitutive transcriptional activity when they are operably linked to said promoter and/or the synthetic upstream element. In particular, the nucleotide sequence of the UAR of the maize Ubi-1 gene is provided and its use in expression cassettes and vectors containing these promoter elements. Cells and plants transformed with these vectors are further provided. These include a transgenic sunflower expressing an exogenous oxalate oxidase gene at a high level under the transcriptional control of a recombinant promoter having at least one upstream activating region of the 35S CaMV promoter.

15 Claims, 11 Drawing Sheets

(SEQ ID NO:3)
5'...TATA(A/T)A(A/T)A.....25bp...........TYYTCAT(A/C)AA.....3'

FIG. 1.

SYN II CORE (64%)
(SEQ ID NO:1)
...GGATCCACTCGAGCGGCTATAAATACGTACCTACGCACGCTGCGCTACCATCCCGAGCACTGCAGTGTCGAC...

CAM35S (40%)
(SEQ ID NO:4)
...CCTCTATATAAGCAAGTTCATTTCATTTGGAGAGGAAACG...

FIG. 2.

RSYN7 (SEQ ID NO:2)
5' GGATCCTATGCGTATGGTATGACGTGTGTTCAAGATGATGACTTCAAACCTACCTATGACGTAT
GGTATGACGTGTGTCGACTGATGACTTAGATC 3'

FIG. 3.

PHP 6086 (5.579 Kb)

| element | sequence | SOURCE | position |
|---|---|---|---|
| AT-rich | TAAT | ATcomconsensus | -140 |
| G-box | CACGTG | tobacco (TAF-1) | -90 |
| Root syn. | TGACGN(7)TGACT | ASF-1 bs | -33/-50 |
| SynII core | | consensus sequence | -50 to +1 |
| CaMV-33 | | CaMV 35S | -33 to +1 |
| Omega prime | | TMV | +1 to +68 |
| Adh1 intron 1 | | Z. mays | +80 to +250 |
| Ga14 BS | | yeast | -90 |

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 72 base pairs
      (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:1:

GGATCCACTC GAGCGGCTAT AAATACGTAC CTACGCACGC TGCGCTACCA TCCCGAGCAC      60

TGCAGTGTCG AC                                                         72

(2) INFORMATION FOR SEQ ID NO:2:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic nucleic acid"

(xi) SEQUENCE DESCRIPTION: SEQ ID NO:2:

GGATCCTATG CGTATGGTAT GACGTGTGTT CAAGATGATG ACTTCAAACC TACCTATGAC      60

GTATGGTATG ACGTGTGTCG ACTGATGACT TAGATC                               96

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TATAWAWATY YTCATMAA                                                   18

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CCTCTATATA AGCAAGTTCA TTTCATTTGG AGAGGAAACG                            40

(2) INFORMATION FOR SEQ ID NO:5:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TGAGC                                                                  5
```

```
(2) INFORMATION FOR SEQ ID NO:6:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(xi) SEQUENCE DESCRIPTION: SEQ ID NO:6:

TCGACACTGC AGCTCTAGGG ATGGTAGCGC AGGGTGCGTA GGTACGTATT TATAGCCGCT      60

CGAGTG                                                                66

(2) INFORMATION FOR SEQ ID NO:7:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(xi) SEQUENCE DESCRIPTION: SEQ ID NO:7:

GATCCACTCG AGCGGCTATA AATACGTACC TACGCACCCT GCGCTACCAT CCCTAGAGCT      60

GCAGTG                                                                66

(2) INFORMATION FOR SEQ ID NO:8:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(xi) SEQUENCE DESCRIPTION: SEQ ID NO:8:

GATCCTATGA CGTATGGTAT GACGTGTGTT CAAGATGATG ACTTCAAACC TACCTATGAC      60

GTATGGTATG ACGTGTGTCG ACTGATGACT TA                                   92

(2) INFORMATION FOR SEQ ID NO:9:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(xi) SEQUENCE DESCRIPTION: SEQ ID NO:9:

GATCTAAGTC ATCAGTCGAC ACACGTCATA CCATACGTCA TAGGTAGGTT TGAAGTCATC      60

ATCTTGAACA CACGTCATAC CATACGTCAT AG                                   92

(2) INFORMATION FOR SEQ ID NO:10:

(i) SEQUENCE CHARACTERISTICS:
        (A) LENGTH: 72 base pairs
        (B) TYPE: nucleic acid
```

(C) STRANDEDNESS: single
            (D) TOPOLOGY: linear (ii) MOLECULE TYPE: other nucleic acid
            (A) DESCRIPTION: /desc = "Synthetic nucleic acid core
                promoter with G/C transversions"

(xi) SEQUENCE DESCRIPTION: SEQ ID NO:10:

GGATCCACTC GAGCGGCTAT AAATASSTAS STASSSASSS TSSSSTASSA TCCCGAGCAC    60

TGCAGTGTCG AC    72

(2) INFORMATION FOR SEQ ID NO:11:

(i) SEQUENCE CHARACTERISTICS:
            (A) LENGTH: 332 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

CGTCAACATG GTGGAGCACG ACACTCTCGT CTACTCCAAG AATATCAAAG ATACAGTCTC    60

AGAAGACCAA AGGGCTATTG AGACTTTTCA ACAAAGGGTA ATATCGGGAA ACCTCCTCGG   120

ATTCCATTGC CCAGCTATCT GTCACTTCAT CAAAAGGACA GTAGAAAAGG AAGGTGGCAC   180

CTACAAATGC CATCATTGCG ATAAAGGAAA GGCTATCGTT CAAGATGCCT CTGCCGACAG   240

TGGTCCCAAA GATGGACCCC CACCCACGAG GAGCATCGTG GAAAAAGAAG ACGTTCCAAC   300

CACGTCTTCA AAGCAAGTGG ATTGATGTGA TG    332

(2) INFORMATION FOR SEQ ID NO:12:

(i) SEQUENCE CHARACTERISTICS:
            (A) LENGTH: 499 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:12:

CGTCAACATG GTGGAGCACG ACACTCTCGT CTACTCCAAG AATATCAAAG ATACAGTCTC    60

AGAAGACCAA AGGGCTATTG AGACTTTTCA ACAAAGGGTA ATATCGGGAA ACCTCCTCGG   120

ATTCCATTGC CCAGCTATCT GTCACTTCAT CAAAAGGACA GTAGAAAAGG AAGGTGGCAC   180

CTACAAATGC CATCATTGCG ATAAAGGAAA GGCTATCGTT CAAGATGCCT CTGCCGACAG   240

TGGTCCCAAA GATGGACCCC CACCCACGAG GAGCATCGTG GAAAAAGAAG ACGTTCCAAC   300

CACGTCTTCA AAGCAAGTGG ATTGATGTGA TGATCCTATG CGTATGGTAT GACGTGTGTT   360

CAAGATGATG ACTTCAAACC TACCTATGAC GTATGGTATG ACGTGTGTCG ACTGATGACT   420

TAGATCCACT CGAGCGGCTA TAAATACGTA CCTACGCACC CTGCGCTACC ATCCCTAGAG   480

CTGCATGCTT ATTTTTACA    499

(2) INFORMATION FOR SEQ ID NO:13:

(i) SEQUENCE CHARACTERISTICS:
            (A) LENGTH: 813 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
        (A) ORGANISM: Zea mays (xi) SEQUENCE DESCRIPTION: SEQ ID NO:13:

| | | | | | |
|---|---|---|---|---|---|
| TCTAGAGATA | ATGAGCATTG | CATGTCTAAG | TTATAAAAAA | TTACCACATA | TTTTTTTTGT | 60 |
| CACACTTGTT | TGAAGTGCAG | TTTATCTATC | TTTATACATA | TATTTAAACT | TTACTCTACG | 120 |
| AATAATATAA | TCTATAGTAC | TACAATAATA | TCAGTGTTTT | AGAGAATCAT | ATAAATGAAC | 180 |
| AGTTAGACAT | GGTCTAAAGG | ACAATTGAGT | ATTTTGACAA | CAGGACTCTA | CAGTTTTATC | 240 |
| TTTTTAGTGT | GCATGTGTTC | TCCTTTTTTT | TTGCAAATAG | CTTCACCTAT | ATAATACTTC | 300 |
| ATCCATTTTA | TTAGTACATC | CATTTAGGGT | TTAGGGTTAA | TGGTTTTTAT | AGACTAATTT | 360 |
| TTTTAGTACA | TCTATTTTAT | TCTATTTTAG | CCTCTAAATT | AAGAAAACTA | AAACTCTATT | 420 |
| TTAGTTTTTT | TATTTAATAA | TTTAGATATA | AAATAGAATA | AAATAAAGTG | ACTAAAAATT | 480 |
| AAACAAATAC | CCTTTAAGAA | ATTAAAAAAA | CTAAGGAAAC | ATTTTTCTTG | TTTCGAGTAG | 540 |
| ATAATGCCAG | CCTGTTAAAC | GCCGTCGACG | AGTCTAACGG | ACACCAACCA | GCGAACCAGC | 600 |
| AGCGTCGCGT | CGGGCCAAGC | GAAGCAGACG | GCACGGCATC | TCTGTCGCTG | CCTCTGGACC | 660 |
| CCTCTCGAGA | GTTCCGCTCC | ACCGTTGGAC | TTGCTCCGCT | GTCGGCATCC | AGAAATTGCG | 720 |
| TGGCGGAGCG | GCAGACGTGA | GCCGGCACGG | CAGGCGGCCT | CCTCCTCCTC | TCACGGCACG | 780 |
| GCAGCTACGG | GGGATTCCTT | TCCCACCGCT | CCT | | | 813 |

(2) INFORMATION FOR SEQ ID NO:14:

(i) SEQUENCE CHARACTERISTICS:
        (A) LENGTH: 1600 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

| | | | | | |
|---|---|---|---|---|---|
| GATCTGAGTC | TAGAAATCCG | TCAACATGGT | GGAGCACGAC | ACTCTCGTCT | ACTCCAAGAA | 60 |
| TATCAAAGAT | ACAGTCTCAG | AAGACCAAAG | GGCTATTGAG | ACTTTTCAAC | AAAGGGTAAT | 120 |
| ATCGGGAAAC | CTCCTCGGAT | TCCATTGCCC | AGCTATCTGT | CACTTCATCA | AAAGGACAGT | 180 |
| AGAAAAGGAA | GGTGGCACCT | ACAAATGCCA | TCATTGCGAT | AAAGGAAAGG | CTATCGTTCA | 240 |
| AGATGCCTCT | GCCGACAGTG | GTCCCAAAGA | TGGACCCCCA | CCCACGAGGA | GCATCGTGGA | 300 |
| AAAAGAAGAC | GTTCCAACCA | CGTCTTCAAA | GCAAGTGGAT | TGATGTGATG | ATCCTATGCG | 360 |
| TATGGTATGA | CGTGTGTTCA | AGATGATGAC | TTCAAACCTA | CCTATGACGT | ATGGTATGAA | 420 |
| CGTGTGTCGA | CTGATGACTT | AGATCCACTC | GAGCGGCTAT | AAATACGTAC | CTACGCACCC | 480 |
| TGCGCTACCA | TCCCTAGAGC | TGCAGCTTAT | TTTTACAACA | ATTACCAACA | ACAACAAACA | 540 |
| ACAAACAACA | TTACAATTAC | TATTTACAAT | TACAGTCGAC | CCGGGATCCA | TGGGGTACTC | 600 |
| CAAAACCCTA | GTAGCTGGCC | TGTTCGCAAT | GCTGTTACTA | GCTCCGGCCG | TCTTGGCCAC | 660 |
| CGACCCAGAC | CCTCTCCAGG | ACTTCTGTGT | CGCCGACCTC | GACGGCAAGG | CGGTCTCGGT | 720 |
| GAACGGGCAC | ACGTGCAAGC | CCATGTCGGA | GGCCGGCGAC | GACTTCCTCT | TCTCGTCCAA | 780 |
| GTTGGCCAAG | GCCGGCAACA | CGTCCACCCC | GAACGGCTCC | GCCGTGACGG | AGCTCGACGT | 840 |
| GGCCGAGTGG | CCCGGTACCA | ACAAGCTGGG | TGGTGTCATG | AACCGCGTGG | ATTTTGGTCC | 900 |

| CGGAGGGACC | AACCCACCAC | ACATCCACCC | GCGTGCCACC | GAGATCGGCA | TCGTGATGAA | 960 |
| AGGTGAGCTT | CTCGTGGGAA | TCCTTGGCAG | CCTCGACTCC | GGGAACAAGC | TCTACTCGAG | 1020 |
| GGTGGTGCGC | GCCGGAGAGA | CGTTCCTCAT | CCCACGGGGC | CTCATGCACT | TCCAGTTCAA | 1080 |
| CGTCGGTAAG | ACCGAGGCCT | CCATGGTCGT | CTCCTTCAAC | AGCCAGAACC | CCGGCATTGT | 1140 |
| CTTCGTGCCC | CTCACGCTCT | TCGGCTCCAA | CCCGCCCATC | CCAACGCCGG | TGCTCACCAA | 1200 |
| GGCACTCCGG | GTGGAGGCCA | GGTCGTGGA | ACTTCTCAAG | TCCAAGTTTG | CCGCTGGGTT | 1260 |
| TTAATTTCTA | GGATCCTCTA | GAGTCGAACC | TAGACTTGTC | CATCTTCTGG | ATTGGCCAAC | 1320 |
| TTAATTAATG | TATGAAATAA | AAGGATGCAC | ACATAGTGAC | ATGCTAATCA | CTATAATGTG | 1380 |
| GGCATCAAAG | TTGTGTGTTA | TGTGTAATTA | CTAGTTATCT | GAATAAAAGA | GAAAGAGATC | 1440 |
| ATCCATATTT | CTTATCCTAA | ATGAATGTCA | CGTGTCTTTA | TAATTCTTTG | ATGAACCAGA | 1500 |
| TGCATTTCAT | TAACCAAATC | CATATACATA | TAAATATTAA | TCATATATAA | TTAATATCAA | 1560 |
| TTGGGTTAGC | AAAACAAATC | TAGTCTAGGT | GTGTTTTGCC | | | 1600 |

(2) INFORMATION FOR SEQ ID NO:15:

(i) SEQUENCE CHARACTERISTICS:
        (A) LENGTH: 994 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

| TCTAGAGATA | ATGAGCATTG | CATGTCTAAG | TTATAAAAAA | TTACCACATA | TTTTTTTTGT | 60 |
| CACACTTGTT | TGAAGTGCAG | TTTATCTATC | TTTATACATA | TATTTAAACT | TTACTCTACG | 120 |
| AATAATATAA | TCTATAGTAC | TACAATAATA | TCAGTGTTTT | AGAGAATCAT | ATAAATGAAC | 180 |
| AGTTAGACAT | GGTCTAAAGG | ACAATTGAGT | ATTTTGACAA | CAGGACTCTA | CAGTTTTATC | 240 |
| TTTTTAGTGT | GCATGTGTTC | TCCTTTTTTT | TTGCAAATAG | CTTCACCTAT | ATAATACTTC | 300 |
| ATCCATTTTA | TTAGTACATC | CATTTAGGGT | TTAGGGTTAA | TGGTTTTTAT | AGACTAATTT | 360 |
| TTTTAGTACA | TCTATTTTAT | TCTATTTTAG | CCTCTAAATT | AAGAAAACTA | AAACTCTATT | 420 |
| TTAGTTTTTT | TATTTAATAA | TTTAGATATA | AAATAGAATA | AAATAAAGTG | ACTAAAAATT | 480 |
| AAACAAATAC | CCTTTAAGAA | ATTAAAAAAA | CTAAGGAAAC | ATTTTTCTTG | TTTCGAGTAG | 540 |
| ATAATGCCAG | CCTGTTAAAC | GCCGTCGACG | AGTCTAACGG | ACACCAACCA | GCGAACCAGC | 600 |
| AGCGTCGCGT | CGGGCCAAGC | GAAGCAGACG | GCACGGCATC | TCTGTCGCTG | CCTCTGGACC | 660 |
| CCTCTCGAGA | GTTCCGCTCC | ACCGTTGGAC | TTGCTCCGCT | GTCGGCATCC | AGAAATTGCG | 720 |
| TGGCGGAGCG | GCAGACGTGA | GCCGGCACGG | CAGGCGGCCT | CCTCCTCCTC | TCACGGCACG | 780 |
| GCAGCTACGG | GGGATTCCTT | TCCCACCGCT | CCTACTAGAA | CTAGTGGATC | CTATGCGTAT | 840 |
| GGTATGACGT | GTGTTCAAGA | TGATGACTTC | AAACCTACCT | ATGACGTATG | GTATGACGTG | 900 |
| TGTCGACTGA | TGACTTAGAT | CCACTCGAGC | GGCTATAAAT | ACGTACCTAC | GCACCCTGCG | 960 |
| CTACCATCCC | TAGAGCTGCA | TGCTTATTTT | TACA | | | 994 |

(2) INFORMATION FOR SEQ ID NO:16:

(i) SEQUENCE CHARACTERISTICS:
        (A) LENGTH: 1807 base pairs
        (B) TYPE: nucleic acid (C) STRANDEDNESS: single
(D) TOPOLOGY: linear (ii) MOLECULE TYPE: other nucleic acid (xi) SEQUENCE DESCRIPTION: SEQ ID NO:16:

```
TCTAGAGATA ATGAGCATTG CATGTCTAAG TTATAAAAAA TTACCACATA TTTTTTTTGT      60
CACACTTGTT TGAAGTGCAG TTTATCTATC TTTATACATA TATTTAAACT TTACTCTACG     120
AATAATATAA TCTATAGTAC TACAATAATA TCAGTGTTTT AGAGAATCAT ATAAATGAAC     180
AGTTAGACAT GGTCTAAAGG ACAATTGAGT ATTTTGACAA CAGGACTCTA CAGTTTTATC     240
TTTTAGTGT GCATGTGTTC TCCTTTTTTT TTGCAAATAG CTTCACCTAT ATAATACTTC      300
ATCCATTTTA TTAGTACATC CATTTAGGGT TTAGGGTTAA TGGTTTTTAT AGACTAATTT     360
TTTTAGTACA TCTATTTTAT TCTATTTTAG CCTCTAAATT AAGAAAACTA AAACTCTATT     420
TTAGTTTTTT TATTTAATAA TTTAGATATA AAATAGAATA AAATAAAGTG ACTAAAAATT     480
AAACAAATAC CCTTTAAGAA ATTAAAAAAA CTAAGGAAAC ATTTTTCTTG TTTCGAGTAG     540
ATAATGCCAG CCTGTTAAAC GCCGTCGACG AGTCTAACGG ACACCAACCA GCGAACCAGC     600
AGCGTCGCGT CGGGCCAAGC GAAGCAGACG GCACGGCATC TCTGTCGCTG CCTCTGGACC     660
CCTCTCGAGA GTTCCGCTCC ACCGTTGGAC TTGCTCCGCT GTCGGCATCC AGAAATTGCG     720
TGGCGGAGCG GCAGACGTGA GCCGGCACGG CAGGCGGCCT CCTCCTCCTC TCACGGCACG     780
GCAGCTACGG GGGATTCCTT TCCCACCGCT CCTACTAGAG ATAATGAGCA TTGCATGTCT     840
AAGTTATAAA AAATTACCAC ATATTTTTTT TGTCACACTT GTTTGAAGTG CAGTTTATCT     900
ATCTTTATAC ATATATTTAA ACTTTACTCT ACGAATAATA TAATCTATAG TACTACAATA     960
ATATCAGTGT TTTAGAGAAT CATATAAATG AACAGTTAGA CATGGTCTAA AGGACAATTG    1020
AGTATTTTGA CAACAGGACT CTACAGTTTT ATCTTTTTAG TGTGCATGTG TTCTCCTTTT    1080
TTTTTGCAAA TAGCTTCACC TATATAATAC TTCATCCATT TTATTAGTAC ATCCATTTAG    1140
GGTTTAGGGT TAATGGTTTT TATAGACTAA TTTTTTTAGT ACATCTATTT TATTCTATTT    1200
TAGCCTCTAA ATTAAGAAAA CTAAAACTCT ATTTTAGTTT TTTTATTTAA TAATTTAGAT    1260
ATAAAATAGA ATAAAATAAA GTGACTAAAA ATTAAACAAA TACCCTTTAA GAAATTAAAA    1320
AAACTAAGGA AACATTTTTC TTGTTTCGAG TAGATAATGC CAGCCTGTTA AACGCCGTCG    1380
ACGAGTCTAA CGGACACCAA CCAGCGAACC AGCAGCGTCG CGTCGGGCCA AGCGAAGCAG    1440
ACGGCACGGC ATCTCTGTCG CTGCCTCTGG ACCCCTCTCG AGAGTTCCGC TCCACCGTTG    1500
GACTTGCTCC GCTGTCGGCA TCCAGAAATT GCGTGGCGGA GCGGCAGACG TGAGCCGGCA    1560
CGGCAGGCGG CCTCCTCCTC CTCTCACGGC ACGGCAGCTA CGGGGGATTC CTTTCCCACC    1620
GCTCCTACTA GAACTAGTGG ATCCTATGCG TATGGTATGA CGTGTGTTCA AGATGATGAC    1680
TTCAAACCTA CCTATGACGT ATGGTATGAC GTGTGTCGAC TGATGACTTA GATCCACTCG    1740
AGCGGCTATA AATACGTACC TACGCACCCT GCGCTACCAT CCCTAGAGCT GCATGCTTAT    1800
TTTTACA                                                              1807
```

(2) INFORMATION FOR SEQ ID NO:17:

(i) SEQUENCE CHARACTERISTICS:
(A) LENGTH: 2620 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:17:

| | | | | | |
|---|---|---|---|---|---|
| TCTAGAGATA | ATGAGCATTG | CATGTCTAAG | TTATAAAAAA | TTACCACATA | TTTTTTTTGT | 60 |
| CACACTTGTT | TGAAGTGCAG | TTTATCTATC | TTTATACATA | TATTTAAACT | TTACTCTACG | 120 |
| AATAATATAA | TCTATAGTAC | TACAATAATA | TCAGTGTTTT | AGAGAATCAT | ATAAATGAAC | 180 |
| AGTTAGACAT | GGTCTAAAGG | ACAATTGAGT | ATTTTGACAA | CAGGACTCTA | CAGTTTTATC | 240 |
| TTTTTAGTGT | GCATGTGTTC | TCCTTTTTTT | TTGCAAATAG | CTTCACCTAT | ATAATACTTC | 300 |
| ATCCATTTTA | TTAGTACATC | CATTTAGGGT | TTAGGGTTAA | TGGTTTTTAT | AGACTAATTT | 360 |
| TTTTAGTACA | TCTATTTTAT | TCTATTTTAG | CCTCTAAATT | AAGAAAACTA | AAACTCTATT | 420 |
| TTAGTTTTTT | TATTTAATAA | TTTAGATATA | AAATAGAATA | AAATAAAGTG | ACTAAAAATT | 480 |
| AAACAAATAC | CCTTTAAGAA | ATTAAAAAAA | CTAAGGAAAC | ATTTTTCTTG | TTTCGAGTAG | 540 |
| ATAATGCCAG | CCTGTTAAAC | GCCGTCGACG | AGTCTAACGG | ACACCAACCA | GCGAACCAGC | 600 |
| AGCGTCGCGT | CGGGCCAAGC | GAAGCAGACG | GCACGGCATC | TCTGTCGCTG | CCTCTGGACC | 660 |
| CCTCTCGAGA | GTTCCGCTCC | ACCGTTGGAC | TTGCTCCGCT | GTCGGCATCC | AGAAATTGCG | 720 |
| TGGCGGAGCG | GCAGACGTGA | GCCGGCACGG | CAGGCGGCCT | CCTCCTCCTC | TCACGGCACG | 780 |
| GCAGCTACGG | GGGATTCCTT | TCCCACCGCT | CCTACTAGAG | ATAATGAGCA | TTGCATGTCT | 840 |
| AAGTTATAAA | AAATTACCAC | ATATTTTTTT | TGTCACACTT | GTTTGAAGTG | CAGTTTATCT | 900 |
| ATCTTTATAC | ATATATTTAA | ACTTTACTCT | ACGAATAATA | TAATCTATAG | TACTACAATA | 960 |
| ATATCAGTGT | TTTAGAGAAT | CATATAAATG | AACAGTTAGA | CATGGTCTAA | AGGACAATTG | 1020 |
| AGTATTTTGA | CAACAGGACT | CTACAGTTTT | ATCTTTTTAG | TGTGCATGTG | TTCTCCTTTT | 1080 |
| TTTTTGCAAA | TAGCTTCACC | TATATAATAC | TTCATCCATT | TTATTAGTAC | ATCCATTTAG | 1140 |
| GGTTTAGGGT | TAATGGTTTT | TATAGACTAA | TTTTTTTAGT | ACATCTATTT | TATTCTATTT | 1200 |
| TAGCCTCTAA | ATTAAGAAAA | CTAAAACTCT | ATTTTAGTTT | TTTTATTTAA | TAATTTAGAT | 1260 |
| ATAAAATAGA | ATAAAATAAA | GTGACTAAAA | ATTAAACAAA | TACCCTTTAA | GAAATTAAAA | 1320 |
| AAACTAAGGA | AACATTTTTC | TTGTTTCGAG | TAGATAATGC | CAGCCTGTTA | AACGCCGTCG | 1380 |
| ACGAGTCTAA | CGGACACCAA | CCAGCGAACC | AGCAGCGTCG | CGTCGGGCCA | AGCGAAGCAG | 1440 |
| ACGGCACGGC | ATCTCTGTCG | CTGCCTCTGG | ACCCCTCTCG | AGAGTTCCGC | TCCACCGTTG | 1500 |
| GACTTGCTCC | GCTGTCGGCA | TCCAGAAATT | GCGTGGCGGA | GCGGCAGACG | TGAGCCGGCA | 1560 |
| CGGCAGGCGG | CCTCCTCCTC | CTCTCACGGC | ACGGCAGCTA | CGGGGGATTC | CTTTCCCACC | 1620 |
| GCTCCTACTA | GAGATAATGA | GCATTGCATG | TCTAAGTTAT | AAAAAATTAC | CACATATTTT | 1680 |
| TTTTGTCACA | CTTGTTTGAA | GTGCAGTTTA | TCTATCTTTA | TACATATATT | TAAACTTTAC | 1740 |
| TCTACGAATA | ATATAATCTA | TAGTACTACA | ATAATATCAG | TGTTTTAGAG | AATCATATAA | 1800 |
| ATGAACAGTT | AGACATGGTC | TAAAGGACAA | TTGAGTATTT | TGACAACAGG | ACTCTACAGT | 1860 |
| TTTATCTTTT | TAGTGTGCAT | GTGTTCTCCT | TTTTTTTGC | AAATAGCTTC | ACCTATATAA | 1920 |
| TACTTCATCC | ATTTTATTAG | TACATCCATT | TAGGGTTTAG | GGTTAATGGT | TTTTATAGAC | 1980 |
| TAATTTTTTT | AGTACATCTA | TTTTATTCTA | TTTTAGCCTC | TAAATTAAGA | AAACTAAAAC | 2040 |
| TCTATTTTAG | TTTTTTTATT | TAATAATTTA | GATATAAAAT | AGAATAAAAT | AAAGTGACTA | 2100 |
| AAAATTAAAC | AAATACCCTT | TAAGAAATTA | AAAAAACTAA | GGAAACATTT | TTCTTGTTTC | 2160 |
| GAGTAGATAA | TGCCAGCCTG | TTAAACGCCG | TCGACGAGTC | TAACGGACAC | CAACCAGCGA | 2220 |

-continued

```
ACCAGCAGCG TCGCGTCGGG CCAAGCGAAG CAGACGGCAC GGCATCTCTG TCGCTGCCTC    2280

TGGACCCCTC TCGAGAGTTC CGCTCCACCG TTGGACTTGC TCCGCTGTCG GCATCCAGAA    2340

ATTGCGTGGC GGAGCGGCAG ACGTGAGCCG GCACGGCAGG CGGCCTCCTC CTCCTCTCAC    2400

GGCACGGCAG CTACGGGGGA TTCCTTTCCC ACCGCTCCTA CTAGAACTAG TGGATCCTAT    2460

GCGTATGGTA TGACGTGTGT TCAAGATGAT GACTTCAAAC CTACCTATGA CGTATGGTAT    2520

GACGTGTGTC GACTGATGAC TTAGATCCAC TCGAGCGGCT ATAAATACGT ACCTACGCAC    2580

CCTGCGCTAC CATCCCTAGA GCTGCATGCT TATTTTTACA                         2620
```

(2) INFORMATION FOR SEQ ID NO:18:

(i) SEQUENCE CHARACTERISTICS:
        (A) LENGTH: 3433 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:18:

```
TCTAGAGATA ATGAGCATTG CATGTCTAAG TTATAAAAAA TTACCACATA TTTTTTTTGT      60

CACACTTGTT TGAAGTGCAG TTTATCTATC TTTATACATA TATTTAAACT TTACTCTACG     120

AATAATATAA TCTATAGTAC TACAATAATA TCAGTGTTTT AGAGAATCAT ATAAATGAAC     180

AGTTAGACAT GGTCTAAAGG ACAATTGAGT ATTTTGACAA CAGGACTCTA CAGTTTTATC     240

TTTTTAGTGT GCATGTGTTC TCCTTTTTTT TTGCAAATAG CTTCACCTAT ATAATACTTC     300

ATCCATTTTA TTAGTACATC CATTTAGGGT TTAGGGTTAA TGGTTTTTAT AGACTAATTT     360

TTTTAGTACA TCTATTTTAT TCTATTTTAG CCTCTAAATT AAGAAAACTA AAACTCTATT     420

TTAGTTTTTT TATTTAATAA TTTAGATATA AAATAGAATA AAATAAAGTG ACTAAAAATT     480

AAACAAATAC CCTTTAAGAA ATTAAAAAAA CTAAGGAAAC ATTTTTCTTG TTTCGAGTAG     540

ATAATGCCAG CCTGTTAAAC GCCGTCGACG AGTCTAACGG ACACCAACCA GCGAACCAGC     600

AGCGTCGCGT CGGGCCAAGC GAAGCAGACG GCACGGCATC TCTGTCGCTG CCTCTGGACC     660

CCTCTCGAGA GTTCCGCTCC ACCGTTGGAC TTGCTCCGCT GTCGGCATCC AGAAATTGCG     720

TGGCGGAGCG GCAGACGTGA GCCGGCACGG CAGGCGGCCT CCTCCTCCTC TCACGGCACG     780

GCAGCTACGG GGGATTCCTT TCCCACCGCT CCTACTAGAG ATAATGAGCA TTGCATGTCT     840

AAGTTATAAA AAATTACCAC ATATTTTTTT TGTCACACTT GTTTGAAGTG CAGTTTATCT     900

ATCTTTATAC ATATATTTAA ACTTTACTCT ACGAATAATA TAATCTATAG TACTACAATA     960

ATATCAGTGT TTTAGAGAAT CATATAAATG AACAGTTAGA CATGGTCTAA AGGACAATTG    1020

AGTATTTTGA CAACAGGACT CTACAGTTTT ATCTTTTTAG TGTGCATGTG TTCTCCTTTT    1080

TTTTTGCAAA TAGCTTCACC TATATAATAC TTCATCCATT TTATTAGTAC ATCCATTTAG    1140

GGTTTAGGGT TAATGGTTTT TATAGACTAA TTTTTTTAGT ACATCTATTT TATTCTATTT    1200

TAGCCTCTAA ATTAAGAAAA CTAAAACTCT ATTTTAGTTT TTTTATTTAA TAATTTAGAT    1260

ATAAAATAGA ATAAAATAAA GTGACTAAAA ATTAAACAAA TACCCTTTAA GAAATTAAAA    1320

AAACTAAGGA AACATTTTTC TTGTTTCGAG TAGATAATGC CAGCCTGTTA AACGCCGTCG    1380

ACGAGTCTAA CGGACACCAA CCAGCGAACC AGCAGCGTCG CGTCGGGCCA AGCGAAGCAG    1440

ACGGCACGGC ATCTCTGTCG CTGCCTCTGG ACCCCTCTCG AGAGTTCCGC TCCACCGTTG    1500

GACTTGCTCC GCTGTCGGCA TCCAGAAATT GCGTGGCGGA GCGGCAGACG TGAGCCGGCA    1560
```

-continued

| | | | | | |
|---|---|---|---|---|---|
| CGGCAGGCGG | CCTCCTCCTC | CTCTCACGGC | ACGGCAGCTA | CGGGGGATTC | CTTTCCCACC | 1620 |
| GCTCCTACTA | GAGATAATGA | GCATTGCATG | TCTAAGTTAT | AAAAAATTAC | CACATATTTT | 1680 |
| TTTTGTCACA | CTTGTTTGAA | GTGCAGTTTA | TCTATCTTTA | TACATATATT | TAAACTTTAC | 1740 |
| TCTACGAATA | ATATAATCTA | TAGTACTACA | ATAATATCAG | TGTTTTAGAG | AATCATATAA | 1800 |
| ATGAACAGTT | AGACATGGTC | TAAAGGACAA | TTGAGTATTT | TGACAACAGG | ACTCTACAGT | 1860 |
| TTTATCTTTT | TAGTGTGCAT | GTGTTCTCCT | TTTTTTTTGC | AAATAGCTTC | ACCTATATAA | 1920 |
| TACTTCATCC | ATTTTATTAG | TACATCCATT | TAGGGTTTAG | GGTTAATGGT | TTTTATAGAC | 1980 |
| TAATTTTTTT | AGTACATCTA | TTTTATTCTA | TTTTAGCCTC | TAAATTAAGA | AAACTAAAAC | 2040 |
| TCTATTTTAG | TTTTTTTATT | TAATAATTTA | GATATAAAAT | AGAATAAAAT | AAAGTGACTA | 2100 |
| AAAATTAAAC | AAATACCCTT | TAAGAAATTA | AAAAAACTAA | GGAAACATTT | TTCTTGTTTC | 2160 |
| GAGTAGATAA | TGCCAGCCTG | TTAAACGCCG | TCGACGAGTC | TAACGGACAC | CAACCAGCGA | 2220 |
| ACCAGCAGCG | TCGCGTCGGG | CCAAGCGAAG | CAGACGGCAC | GGCATCTCTG | TCGCTGCCTC | 2280 |
| TGGACCCCTC | TCGAGAGTTC | CGCTCCACCG | TTGGACTTGC | TCCGCTGTCG | GCATCCAGAA | 2340 |
| ATTGCGTGGC | GGAGCGGCAG | ACGTGAGCCG | GCACGGCAGG | CGGCCTCCTC | CTCCTCTCAC | 2400 |
| GGCACGGCAG | CTACGGGGGA | TTCCTTTCCC | ACCGCTCCTA | CTAGAGATAA | TGAGCATTGC | 2460 |
| ATGTCTAAGT | TATAAAAAAT | TACCACATAT | TTTTTTTGTC | ACACTTGTTT | GAAGTGCAGT | 2520 |
| TTATCTATCT | TTATACATAT | ATTTAAACTT | TACTCTACGA | ATAATATAAT | CTATAGTACT | 2580 |
| ACAATAATAT | CAGTGTTTTA | GAGAATCATA | TAAATGAACA | GTTAGACATG | GTCTAAAGGA | 2640 |
| CAATTGAGTA | TTTTGACAAC | AGGACTCTAC | AGTTTTATCT | TTTTAGTGTG | CATGTGTTCT | 2700 |
| CCTTTTTTTT | TGCAAATAGC | TTCACCTATA | TAATACTTCA | TCCATTTTAT | TAGTACATCC | 2760 |
| ATTTAGGGTT | TAGGGTTAAT | GGTTTTTATA | GACTAATTTT | TTTAGTACAT | CTATTTTATT | 2820 |
| CTATTTTAGC | CTCTAAATTA | AGAAAACTAA | AACTCTATTT | TAGTTTTTTT | ATTTAATAAT | 2880 |
| TTAGATATAA | AATAGAATAA | AATAAAGTGA | CTAAAAATTA | AACAAATACC | CTTTAAGAAA | 2940 |
| TTAAAAAAAC | TAAGGAAACA | TTTTTCTTGT | TTCGAGTAGA | TAATGCCAGC | CTGTTAAACG | 3000 |
| CCGTCGACGA | GTCTAACGGA | CACCAACCAG | CGAACCAGCA | GCGTCGCGTC | GGGCCAAGCG | 3060 |
| AAGCAGACGG | CACGGCATCT | CTGTCGCTGC | CTCTGGACCC | CTCTCGAGAG | TTCCGCTCCA | 3120 |
| CCGTTGGACT | TGCTCCGCTG | TCGGCATCCA | GAAATTGCGT | GGCGGAGCGG | CAGACGTGAG | 3180 |
| CCGGCACGGC | AGGCGGCCTC | CTCCTCCTCT | CACGGCACGG | CAGCTACGGG | GGATTCCTTT | 3240 |
| CCCACCGCTC | CTACTAGAAC | TAGTGGATCC | TATGCGTATG | GTATGACGTG | TGTTCAAGAT | 3300 |
| GATGACTTCA | AACCTACCTA | TGACGTATGG | TATGACGTGT | GTCGACTGAT | GACTTAGATC | 3360 |
| CACTCGAGCG | GCTATAAATA | CGTACCTACG | CACCCTGCGC | TACCATCCCT | AGAGCTGCAT | 3420 |
| GCTTATTTTT | ACA | | | | | 3433 |

SYNTHETIC PROMOTERS

RELATED APPLICATIONS

This application is a continuation-in-part of U.S. patent application Ser. No. 08/661,601, filed on Jun. 11, 1996 now abandoned, herein incorporated by reference.

FIELD OF THE INVENTION

This invention relates generally to the field of plant molecular biology and in particular to enhanced expression of desired structural genes in both monocotyledonous and dicotyledonous plants.

BACKGROUND OF THE INVENTION

Gene expression encompasses a number of steps originating from the DNA template ultimately to the final protein or protein product. Control and regulation of gene expression can occur through numerous mechanisms. The initiation of transcription of a gene is generally thought of as the predominant control of gene expression. The transcriptional controls (or promoters) are generally relegated to relatively short sequences imbedded in the 5'-flanking or upstream region of the transcribed gene. There are DNA sequences which affect gene expression in response to environmental stimuli, nutrient availability, or adverse conditions including heat shock, anaerobiosis or the presence of heavy metals. There are also DNA sequences which control gene expression during development or in a tissue, or organ specific fashion.

Promoters contain the signals for RNA polymerase to begin transcription so that protein synthesis can proceed. DNA binding, nuclear proteins interact specifically with these cognate promoter DNA sequences to promote the formation of the transcriptional complex and eventually initiate the gene expression process.

One of the most common sequence motifs present in the promoters of genes transcribed by eukaryotic RNA polymerase II (polII) system is the "TATA" element which resides upstream of the start of transcription. Eukaryotic promoters are complex and are comprised of components which include a TATA box consensus sequence at about 35 base pairs 5' relative to the transcription start site or cap site which is defined as +1. The TATA motif is the site where the TATA-binding-protein (TBP) as part of a complex of several polypeptides (TFIID complex) binds and productively interacts (directly or indirectly) with factors bound to other sequence elements of the promoter. This TFIID complex in turn recruits the RNA polymerase II complex to be positioned for the start of transcription generally 25 to 30 base pairs downstream of the TATA element and promotes elongation thus producing RNA molecules. The sequences around the start of transcription (designated INR) of some polI genes seem to provide an alternate binding site for factors that also recruit members of the TFIID complex and thus "activate" transcription. These INR sequences are particularly relevant in promoters that lack functional TATA elements providing the core promoter binding sites for eventual transcription. It has been proposed that promoters containing both a functional TATA and INR motif are the most efficient in transcriptional activity. (Zenzie-Gregory et al, 1992. J. Biol. Chem. 267:2823–2830).

In most instances sequence elements other than the TATA motif are required for accurate transcription. Such elements are often located upstream of the TATA motif and a subset may have homology to the consensus sequence CCAAT.

Other DNA sequences have been found to elevate the overall level of expression of the nearby genes. One of the more common elements that have been described reside far upstream from the initiation site and seem to exhibit position and orientation independent characteristics. These far upstream elements have been designated enhancers.

One of the less common elements by virtue of their specificities are sequences that interact with specific DNA binding factors. These sequence motifs are collectively known as upstream elements which are usually position and orientation dependent.

Many upstream elements have been identified in a number of plant promoters based initially on function and secondarily on sequence homologies. These promoter upstream elements range widely in type of control: from environmental responses like temperature, moisture, wounding, etc., developmental cues, (germination, seed maturation, flowering, etc.) to spatial information (tissue specificity). These elements also seem to exhibit modularity in that they may be exchanged with other elements while maintaining their characteristic control over gene expression.

Promoters are usually positioned 5' or upstream relative to the start of the coding region of the corresponding gene, and the entire region containing all the ancillary elements affecting regulation or absolute levels of transcription may be comprised of less than 100 base pairs or as much as 1 kilobase pair.

A number of promoters which are active in plant cells have been described in the literature. These include nopaline synthase (NOS) and octopine synthase (OCS) promoters (which are carried on tumor inducing plasmids of Agrobacterium tumefaciens). The cauliflower mosaic virus (CaMV) 19S and 35S promoters, the light-inducible promoter from the small subunit of ribulose bisphosphate carboxylase (ssRUBICSO, a very abundant plant polypeptide), and the sucrose synthase promoter are also included. All of these promoters have been used to create various types of DNA constructs which have been expressed in plants. (See for example PCT publication WO84/02913 Rogers, et al).

Two promoters that have been widely used in plant cell transformations are those of the genes encoding alcohol dehydrogenase, AdhI and AdhII. Both genes are induced after the onset of anaerobiosis. Maize AdhI has been cloned and sequenced as has been AdhII. Formation of an AdhI chimeric gene, Adh-Cat comprising the AdhI promoter links to the chloramphenicol acetyltransferase (CAT) coding sequences and nopaline synthase (NOS) 3' signal caused CAT expression at approximately 4-fold higher levels at low oxygen concentrations than under control conditions. Sequence elements necessary for anaerobic induction of the ADH-CAT chimeric have also been identified. The existence of anaerobic regulatory element (ARE) between positions −140 and −99 of the maize AdhI promoter composed of at least two sequence elements positions −133 to −124 and positions −113 to 99 both of which have found to be necessary and are sufficient for low oxygen expression of ADH-CAT gene activity. The Adh promoter however responds to anaerobiosis and is not a constitutive promoter drastically limiting its effectiveness.

Another commonly used promoter is the 35S promoter of Cauliflower Mosaic Virus. The (CaMV) 35S promoter is a dicot virus promoter however it directs expression of genes introduced into protoplasts of both dicots and monocots. The 35S promoter is a very strong promoter and this accounts for its widespread use for high level expression of traits in transgenic plants. The CaMV35S promoter however has also demonstrated relatively low activity in several agriculturally significant graminaceous plants such as wheat. While these promoters all give high expression in dicots, few give high levels of expression in monocots. A need exists for a synthetic promoters and other elements that induce expression in transformed monocot protoplast cells.

SUMMARY OF THE INVENTION

Methods and compositions for the expression of heterologous sequences in host cells are provided. The compositions find particular use in controlling the expression of sequences in plants. The compositions of the invention comprise promoter sequences. In particular, a novel synthetic core promoter molecule and regulatory elements useful in controlling expression in target cells are provided. The core promoter comprises a TATA box and a start of transcription. Further, the "TATA to start" region is 64% or greater GC rich. The regulatory elements include a novel upstream element and upstream activating regions. The upstream activating region is different from the synthetic upstream element. The elements can be used together or with other promoter elements to control expression of sequences of interest.

It is a primary object of the invention to provide synthetic regulatory elements that enhance expression of introduced genes in plant cells and plant tissues.

It is an object of the invention to provide a recombinant promoter molecule that provides for reliably high levels of expression of introduced genes in target cells. It is yet another object of the invention to provide heterologous upstream enhancer elements that can enhance the activity of any promoter.

It is yet another object of the invention to provide plants, plant cells and plant tissues containing either or both of the recombinant promoter or upstream element of the invention.

It is yet another object of the invention to provide vehicles for transformation of plant cells including viral or plasmid vectors and expression cassettes incorporating the synthetic promoter and upstream elements of the invention.

It is yet another object of the invention to provide bacterial cells comprising such vectors for maintenance, and plant transformation.

Other objects of the invention will become apparent from the description of the invention which follows.

DESCRIPTION OF THE FIGURES

FIG. 1 is a depiction of a typical nucleotide base arrangement of a core promoter containing the consensus sequences of TATA and INR motifs present in plant promoters. A designates +1 of the transcribed region.

FIG. 2 is a depiction of the complete Syn II Core Promoter Sequence with an example of a plant promoter and both are aligned at the major start of transcription (bold letter). The TATA motif is underlined. The CaMV 35S promoter is shown with percent GC content sequences shown in parentheses.

FIG. 3 is the DNA sequence of the Rsyn 7 upstream element. The TGACG motifs are indicated in bold.

DETAILED DESCRIPTION OF THE INVENTION

Figure 4:
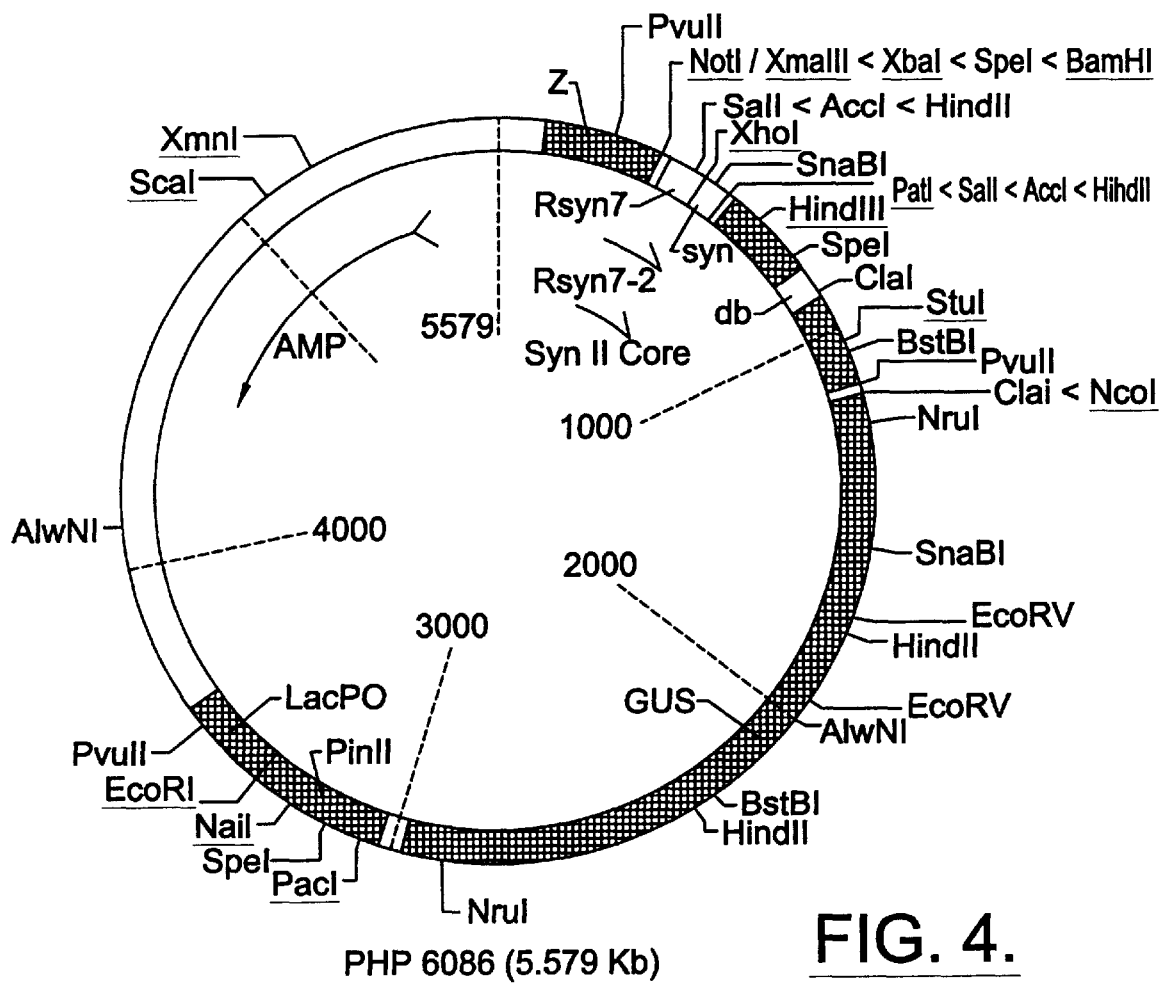
FIG. 4 is a plasmid map of one embodiment of the invention comprising the Syn II Core promoter and Rsyn7 elements driving a GUS containing construct.

In the description that follows a number of terms are used extensively. The following definitions are provided in order to remove ambiguities in the intent or scope of their usage in the specification and claims, and to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically a promoter is located in the 5' region of a gene, proximal to the transcriptional start site of a structural gene. The promoter of the invention comprises at least a core promoter as defined below. Additionally, the promoter may also include at least one upstream elements. Such elements include UARs and optionally, other DNA sequences that affect transcription of a structural gene such as a synthetic upstream element.

A core promoter or minimal promoter contains the essential nucleotide sequences for expression of the operably linked coding sequence, including the TATA box and start of transcription. By this definition, a core promoter may or may not have detectable activity in the absence of specific sequences that may enhance the activity or confer tissue specific activity. For example, the maize SGB6 gene core promoter consists of about 37 nucleotides 5' of the transcriptional start site of the SGB6 gene, while the Cauliflower Mosaic Virus (CaMV) 35S core promoter consists of about 33 nucleotides 5' of the transcriptional start site of the 35S genome.

ADH refers generally to a plant expressible alcohol dehydrogenase gene and specifically to the alcohol dehydrogenase gene from maize.

ADH 1 UAR refers to the DNA fragment spanning the region between nucleotide positions about −1094 to about −106 of the alcohol dehydrogenase gene 1 from maize, or homologous fragment that is functionally equivalent. The sequence is numbered with the start of transcription site designated as +1 according to the correction published by Ellis et al. (1987) supra.

"TATA to start" shall mean the sequence between the primary TATA motif and the start of transcription.

A synthetic DNA is an artificially created DNA sequence that is not produced naturally, and must be introduced to an organism or to an ancestor of that organism to control or to be expressed.

OCS element refers to the TGACG motif identified from the octopine synthase gene, histone genes, enzyme genes for agropine biosynthesis, the mannopine synthase gene, the CaMV 35S gene, histone H3 gene and nopaline synthase gene. As used herein the term includes any sequence capable of binding the ASF-1 factor as identified in U.S. Pat. No. 4,990,607 by Katagiri, the disclosure of which is incorporated by reference.

UAR is typically a position or orientation dependent element that primarily directs tissue, cell type, or regulated expression.

An enhancer is a DNA regulatory element that can increase efficiency of transcription regardless of the distance or orientation of the enhancer relative to the start site of transcription.

The term expression refers to biosynthesis of a gene product. In the case of a structural gene, expression involves transcription of the structural gene into mRNA and then translation of the mRNA into one or more polypeptides.

A cloning vector is a DNA molecule such as a plasmid, cosmid or bacterial phage that has the capability of replicating autonomously in a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

An expression vector is a DNA molecule comprising a gene that is expressed in a host cell. Typically gene expression is placed under the control of certain regulatory elements including promoters, tissue specific regulatory elements, and enhancers. Such a gene is said to be "operably linked to" the regulatory elements.

A recombinant host may be any prokaryotic or eukaryotic cell that contains either a cloning vector or an expression vector. This term also includes those prokaryotic or eukaryotic cells that have been genetically engineered to contain the cloned genes in the chromosome or genome of the host cell.

A transgenic plant is a plant having one or more plant cells that contain an expression vector.

It will be understood that there may be minor sequence variations within sequence or fragments used or disclosed in this application. By "minor variations" is intended that the sequences have at least 80%, preferably 90% sequence identity. These variations may be determined by standard techniques to enable those of ordinary skill in the art to manipulate and bring into utility the functional units of the promoter elements necessary to direct initiation of transcription in the structural gene followed by a plant expressible transcription termination (and perhaps polyadenylation) signal.

Plant tissue includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

One embodiment of the invention, the core promoter, is shown in SEQ ID NO:1. The core promoter is capable of driving expression of a coding sequence in a target cell, particularly plant cells. The core promoter finds use in driving expression of sequences which are only needed at minimal levels in the target cells. Also disclosed is a novel upstream element, SEQ ID NO:2 that helps to potentiate transcription. The synthetic core promoter can be used with combinations of enhancer, upstream elements, and/or activating sequences from the 5'-flanking regions of plant expressible structural genes. Similarly the upstream element can be used in combination with various plant core promoter sequences. In one embodiment the core promoter and upstream element are used together to obtain ten-fold higher expression of an introduced marker gene in monocot transgenic plants than is obtained with the maize ubiquitin 1 promoter.

The core promoter comprises a TATA motif and a GC rich "TATA to start of transcription" region (64% or greater GC content that is generally characteristic of animal promoters. The sequence is placed 5' of a structural gene and will promote constitutive expression which is non-tissue specific in transgenic plant cells.

The invention also comprises an expression cassette comprising (the upstream element) the synthetic core promoter, a structural gene, the expression of which is desired in plant cells, and a polyadenylation or stop signal. The expression cassette can be encompassed in plasmid or viral vectors for transformation of plant protoplast cells.

The invention also encompasses transformed bacterial cells for maintenance and replication of the vector, as well as transformed monocot or dicot cells and ultimately transgenic plants.

In another embodiment, the invention encompasses an upstream element that can be used in combination with the synthetic promoter or with other known promoters in the art. The upstream element comprises at least 3 OCS binding motifs (TGACG) with a novel intervening sequence. One embodiment is disclosed in SEQ ID NO:2 and is placed 5' to a core promoter sequence to enhance the transcription levels of the resulting gene product. Thus the invention comprises an expression cassette comprising the synthetic upstream element of the invention, 5' to a plant inducible promoter which is 5' to a structural gene. This expression cassette can be embodied in vectors and plasmids as earlier described.

In a preferred embodiment the synthetic upstream element is used in combination with the synthetic core promoter sequence to achieve non-tissue specific constitutive expression of the gene product which is a ten-fold enhancement of the maize Ubi-1 promoter.

The present invention also encompasses a promoter construct comprising the synthetic core promoter described above and an upstream activating region. The upstream activating region is different from the synthetic upstream element. Preferably the upstream activating region is an upstream activating region (UAR) having substantial sequence similarity to the UAR of CaMV 35S or maize Ubi-1. Promoter constructs of the invention may comprise the synthetic core promoter in combination with at least one UAR and optionally at least one synthetic upstream element.

The promoter construct can be contained for convenience in an expression cassette. This expression cassette can be embodied in transformation vectors.

The sequence of the upstream activating region (UAR) of the maize Ubi-1 gene is also provided. This UAR can be used in combination with any core promoter to enhance the activity of the promoter.

The promoter of the invention as seen in SEQ ID NO: 1 and/or SEQ ID NO:10 (modified core promoter), can be used to obtain high levels of expression of structural genes. Similarly the upstream element of the invention (SEQ ID NO:2) can be used in combination with other promoters or the promoter of the invention to potentiate levels of transcription in genetically modified plants. Production of a genetically modified plant tissue expressing a structural gene under the control of the regulatory elements of the invention combines teachings of the present disclosure with a variety of techniques and expedients known in the art. In most instances alternate expedients exist for each stage of the overall process. The choice of expedients depends on the variables such as the plasmid vector system chosen for the cloning and introduction of the recombinant DNA molecule, the plant species to be modified, the particular structural gene, promoter elements and upstream elements used. Persons skilled in the art are able to select and use appropriate alternatives to achieve functionality. Culture conditions for expressing desired structural genes and cultured cells are known in the art. Also as known in the art, a number of both monocotyledonous and dicotyledonous plant species are transformable and regenerable such that whole plants containing and expressing desired genes under regulatory control of the promoter molecules and upstream elements of the invention may be obtained. As is known to those of skill in the art, expression in transformed plants may be tissue specific and/or specific to certain developmental stages or environmental influences. Truncated promoter selection and structural gene selection are other parameters which may be optimized to achieve desired plant expression as is known to those of skill in the art and taught herein.

The nucleotide sequences of the invention can be introduced into any plant. The genes to be introduced can be conveniently used in expression cassettes for introduction and expression in any plant of interest.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al., (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639.

The genes of the invention are provided in expression cassettes for expression in the plant of interest. The cassette will include 5' and 3' regulatory sequences operably linked to the gene of interest. The cassette may additionally contain at least one additional gene to be cotransformed into the organism. Alternatively, the additional gene(s) can be provided on another expression cassette. Where appropriate, the gene(s) may be optimized for increased expression in the transformed plant. That is, the genes can be synthesized using plant preferred codons for improved expression. Methods are available in the art for synthesizing plant preferred genes. See, for example, U.S. Pat. Nos. 5,380,831, 5,436, 391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The selection of an appropriate expression vector will depend upon the method of introducing the expression vector into host cells. Typically an expression vector contains (1) prokaryotic DNA elements coding for a bacterial replication origin and an antibiotic resistance gene to provide for the amplification and selection of the expression vector in a bacterial host; (2) DNA elements that control initiation of transcription such as a promoter; (3) DNA elements that control the processing of transcripts such as introns, transcription termination/polyadenylation sequence; and (4) a reporter gene that is operatively linked to the DNA elements to control transcription initiation. Useful reporter genes include β-glucuronidase, β-galactosidase, chloramphenicol acetyl transferase, luciferase, green fluorescent protein (GFP) and the like. Preferably the reporter gene is either β-glucuronidase (GUS), GFP or luciferase. The general descriptions of plant expression vectors and reporter genes can be found in Gruber, et al., "Vectors for Plant Transformation, in Methods in Plant Molecular Biology & Biotechnology" in Glich et al., (Eds. pp. 89–119, CRC Press, 1993). Moreover GUS expression vectors and GUS gene cassettes are available from Clonetech Laboratories, Inc., Palo Alto, Calif. while luciferase expression vectors and luciferase gene cassettes are available from Promega Corp. (Madison, Wis.).

Expression vectors containing genomic or synthetic fragments can be introduced into protoplasts or into intact tissues or isolated cells. Preferably expression vectors are introduced into intact tissue. General methods of culturing plant tissues are provided for example by Maki et al. "Procedures for Introducing Foreign DNA into Plants" in Methods in Plant Molecular Biology & Biotechnology, Glich et al. (Eds. pp. 67–88 CRC Press, 1993); and by Phillips et al. "Cell-Tissue Culture and In-Vitro Manipulation" in Corn & Corn Improvement, 3rd Edition Sprague et al. (Eds. pp. 345–387) American Society of Agronomy Inc. et al. 1988.

Methods of Introducing expression vectors into plant tissue include the direct infection or co-cultivation of plant cell with *Agrobacterium tumefaciens*, Horsch et al., Science, 227:1229 (1985). Descriptions of Agrobacterium vector systems and methods for Agrobacterium-mediated gene transfer provided by Gruber, et al. supra.

Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. "Direct DNA transfer into intact plant cells via microprojectile bombardment" In: Gamborg and Phillips (Eds.) Plant Cell, Tissue and Organ Culture: Fundamental Methods, Springer-Verlag, Berlin (1995).

The vectors of the invention can not only be used for expression of structural genes but may also be used in exon-trap cloning, or promoter trap procedures to detect differential gene expression in varieties of tissues, K. Lindsey et al., 1993 "Tagging Genomic Sequences That Direct Transgene Expression by Activation of a Promoter Trap in Plants", Transgenic Research 2:33–47. D. Auch & Reth, et al., "Exon Trap Cloning: Using PCR to Rapidly Detect and Clone Exons from Genomic DNA Fragments", Nucleic Acids Research, Vol. 18, No. 22, p. 6743.

This inventive promoter is based in part on the discovery that a GC rich "TATA to start" region in a plant promoter acts as a very strong nontissue specific core promoter inducing constitutive expression in plant cells. The TATA element of plant promoters of polI genes generally have the sequence TATA(A/T)A(A/T)A, SEQ ID NO:3, whereas the consensus of the start of transcription consists of the sequence 5'...TYYTCAT(A/C)AA..3'. SEQ ID NO.:3, where the A designates the starting base for transcription. The typical plant promoter sequence is depicted in FIG. 1.

Sequences intervening the TATA element and the start of transcription have been shown to play a significant role in transcriptional activation efficiency. The TATA binding protein has been shown to interact with the minor groove of the double helix binding to the TATA motif bending it towards the major groove side (Kim, et al. 1993, Nature, 365:512–520). It thus follows that sequences downstream of the TATA motif that impact this finding will affect the efficiency of stable transcriptional complex formation and ultimately expression. Surveys of the "TATA to start" regions of plant promoters show a significantly higher level of AT-rich sequences leading to the potential of minor groove compression (Yaurawj et al Biological Abstracts Vol. 47, Issue 8, Ref 144712, "Consensus Sequences for Plant Minimal Promoters" Annual Meeting of the American Society of Plant Physiologists, Jul. 29–Aug. 2, 1995, Plant Physiology 108 [2 Supp.] 1995, 114). Generally animal promoters show a GC-rich "TATA to start" sequence that leads to a major groove compression suggesting that average plant and animal core promoter transcriptional complexes recognize and interact with a somewhat different TATA to start structure with the corresponding sequence difference. Quite surprisingly the applicant has found that a GC-rich animal type synthetic promoter works very well in plants.

While the invention is not bound by any theory, it is possible that the AT-rich TATA motif present in a GC-rich sequence may "present itself" more prominently to the TATA-binding complex by a sharp demarcation of the TATA motif that would interact more tightly with the TATA-binding complex. This would improve the start of transcription efficiency, by shifting the equilibria of binding to a more stabilized form, whereas the "non-bounded TATA" version, i.e. having a higher level of AT-Rich sequences flanking the TATA motif, the TATA-binding complex would potentially slide or stutter 5' or 3' to the start site and effectively reduce the efficiency of binding ultimately reducing transcription. Little data regarding this region of plant promoters is available except crude deletions and some point mutations. The obvious design of a synthetic core promoter for plant expression would include the AT-rich "TATA to start" sequence based on surveys of known supplant promoters. However, based on the "bounded" mechanism, it is postulated by the mechanism of the invention that a more efficient core promoter is a result of a TATA motif imbedded in a GC-rich sequence.

FIG. 2 depicts the Syn II Core promoter sequence, SEQ ID NO:1 of the invention with examples of plant core promoters aligned to the major start of transcription. Another example of a plant promoter 35S of CaMV (SEQ ID NO:4) are shown with percent GC-rich sequences shown at the right in parentheses. The Syn II Core sequence does not show any significant sequence homology to sequences in the public sequence databases.

The synthetic Syn II Core promoter sequence shows a 64% GC-rich "TATA to start" sequence different from the overall 40% GC-rich sequence present in traditional plant promoters (CaMV35S for example). The naturally occurring and isolated UBI core promoter which potentiates very high levels of activity in monocots usually shows a 64% GC-rich "TATA to start" sequence more similar to animal promoters. Such examples provided the impetus to design a high GC-rich "TATA to start" sequence for efficient transcription in opposition to the current dogma of plant core promoters.

Thus the invention comprises a synthetic plant core promoter sequence comprising a TATA motif and a "TATA to start" region that is 64% GC-rich or greater. In a preferred embodiment, the promoter may include restriction endonuclease target sites for ease of cloning. In the most preferred embodiment, the sequence is that of SEQ ID NO:1. As will be appreciated by those of skill in the art, several base transversions within SEQ ID NO:1 may occur which will maintain the percent GC-content and are intended within the scope of this invention. For example guanines could be replaced with cytosines and vice-versa without affecting the overall efficacy of the promoter, so long as the percent GC-content is maintained.

In another embodiment, the invention comprises a synthetic upstream element positioned 5' to any naturally occurring or synthetic promoter for use in plants, particularly maize gene expression.

From the activity of numerous promoters, basic elements (binding sites) have been defined. These include for example AT-rich regions from heat shock promoters, and ASF-1 binding site (AS-1) elements present in octopine synthase (OCS) and Cauliflower Mosaic Virus promoters. AS-1 is one of the better known upstream elements and its binding sequence (OCS element) is present in many constitutive plant promoters such as the CaMV35S, *A. tumefaciens*, NOS and OCS wheat histone promoters. The OCS element was first isolated as an enhancer element in the promoter of the OCS gene where it was identified as a 16-base pair palindromic sequence (Ellis et al., (1987) *EMBO J*. 6:11–16), but has been reduced to its essential features as a TGACG motif. See U.S. Pat. No. 4,990,607 incorporated herein by reference. The upstream element of the invention has a 71% identity to the promoter enhancer element disclosed in U.S. Pat. No. 5,023,179 to Lam et al. The two sequences are quite different in their flanking sequences surrounding the TGACG motif, which regions have been shown to impact the level of transcription enhancement. The transcriptional enhancing activity of the OCS element correlates with the in-vitro binding of a transcriptional factor. Similar elements were also identified in the promoter regions of six other cDNA genes involved in opine synthesis and three plant viral promoters including the CaMV 35S promoter (Bouchez et al. 1989) supra. These elements were shown to bind the OCS transcription factor in-vitro and enhance transcription in plant cells.

In tobacco a DNA binding factor, TGA I, was shown to interact specifically with the AS-1 element either alone or in conjunction with other promoter elements. (Katagiri et al. 1989, Nature 340:727–730). This factor was also shown to be expressed in a root-preferred manner in tobacco plants. Core promoters with one or two copies of the OCS upstream element tend to potentiate gene expression whereas 4 or more repeats of this element produce more or less constitutive activity albeit low relative to intact 35S promoters.

Thus the invention incorporates a synthetic upstream element which can be used with the core promoter of the invention or other core promoters to enhance gene expression. The element incorporates three OCS-like motifs and novel intervening sequences which enhance gene expression.

FIG. 3, SEQ ID NO:2 shows the complete sequence of one embodiment (RSyn7) of the synthetic upstream element which incorporates at least three TGACG SEQ ID NO:5 OSC-like motifs which are indicated in bold.

Sequences flanking many elements such as the TGACG SEQ ID NO:5 motif have been shown to have profound impacts on binding affinities of DNA binding factors and thus play as an important role as the central motifs themselves. (Burrows et al. 1992, Plant Molecular Biology 19:665–675, Shinder et al. 1992, Plant Cell 4:1309–1319, Foster et al. 1994, FASEBJ 8:192–200). The novel sequences flanking the TGACG motifs in the Rsyn7 promoter have been determined and established clear enhancement of transcriptional activity with various promoters, particularly when used with the Syn II Core promoter.

Rsyn7 upstream element has been cloned upstream of the Syn II Core promoter driving a GUS construct and has yielded levels of GUS activity in transgenic maize plants approximately ten-fold higher than the ubiquitin promoter, the strongest maize promoter to date.

In yet another aspect of the present invention, at least one upstream activating region (UAR), which is different from the synthetic upstream element, is operably linked to the synthetic core promoter. The UAR may be used alone or in combination with the synthetic upstream element described herein. Preferably, the upstream activating regions of the cauliflower mosaic virus (CaMV) 35S promoter and the maize Ubi-1 gene promoter are utilized. Additionally, sequences having sequence similarity to these UARs may be utilized as long as such sequences retain the ability to enhance promoter activity. Enhancement can be measured by assaying for levels of transcripts or alternatively protein production.

CaMV 35S UARs have been well studied in the art. The complete nucleotide sequence of the CaMV circular double-strand DNA has been established in the art. See Guilley et al. (1980) Cell 21:285–294. The 35S promoter transcribes the major 35S RNA transcript from the circular viral genome by nucleus RNA polymerase II. See Guilley et al. (1982) Cell 30:763–773. Moreover, the 35S UARs can function with a heterologous promoter and increase expression of a gene of interest in cells and transgenic plants. Shah et al. (1986) Science 233:478–481. Multiple cis regulatory elements for the activity of the CaMV 35S promoter have been identified. See Odell et al. (1985) Nature 313:810–812; Fang et al. (1989) Plant Cell 1:141–150.

In the present invention, a large fragment of the upstream activating regions (UARs) of the CaMV 35S promoter can be utilized to enhance the activity of the core synthetic promoter. The size of the UAR can, for example, range from about 15 base pairs to about 850 base pairs, preferably from about 20 to about 500, more preferably from about 20–25 to about 50–200 base pairs. A preferred region of the 35S CaMV upstream region includes sequences from about −421 to about −90. It is recognized that modifications, in length and nucleotide sequence can be made to the region and still result in enhanced activity of the core synthetic promoter. Such modifications can be tested for effect on activity by using expression systems as set forth in the Experimental Section of the present application. The numbers on the UAR sequence diagram indicate the position upstream from the transcription start site, or +1 position of the 35S structural gene. For example, −25 means a position 25 base pairs upstream from the transcription start site of the 35S structural gene.

The upstream activating region of the maize ubiquitin gene Ubi-1 can also be utilized in the invention. The sequence of the Ubi-1 gene transcription regulatory region is disclosed in U.S. Pat. No. 5,510,474. See also Christensen et al. (1992) Plant Mol. Biol. 18:675–689; Cornejo et al. (1993) Plant Mol. Biol. 23:567–581; Takimoto et al. (1994) Plant Mol. Biol. 26:1007–1012; and Christensen et al. (1996) Transgenic Res. 5:213–218. The UAR of the Ubi-1 gene promoter comprises preferably from about −867 to about −54. As indicated above for the 35S UAR, modifications of the Ubi-1 UAR that still function to enhance the activity of the core promoter are encompassed.

While the full sequence of the ubiquitin promoter has been published, this is the first disclosure of the Ubi UAR. Thus, the invention discloses the UAR of the ubiquitin promoter as well as the Ubi UAR in combination with any promoter. Additionally, methods for using the Ubi UAR to enhance activity of promoters are encompassed.

The upstream activating regions as described herein can be linked with the synthetic core promoter and/or other upstream elements by any conventional method that is generally known in the art as long as an operative element or promoter is constructed. The upstream activating regions are generally operably linked to the 5' end of the core promoter. When the synthetic upstream element is also present, the upstream activating regions can be linked to either the 5' end of the synthetic upstream element, the 3' end of the core synthetic promoter or inserted between the synthetic upstream element and the synthetic core promoter. In a preferred embodiment the upstream activating regions are linked in close proximity to the synthetic upstream element, if present, and the synthetic core promoter. By close proximity is intended within from about 1 to about 50 nucleotides. However, it is recognized that more than 50 nucleotides may separate the elements. The upstream activating regions can be in the 5' to 3' direction or the 3' to 5' direction, but preferably in the 5' to 3' direction at the 5' end of the synthetic core promoter or the synthetic upstream element.

One or multiple copies of the upstream activating regions can be used. When multiple copies are utilized, they can be tandem repeats of one UAR or combinations of several UARs. In this manner, the level of expression of a nucleotide sequence of interest can be controlled by the number of UARs present in the promoter construction since the results indicate that increased expression levels are obtained with increased numbers of UARs. Thus, the invention provides methods for regulating levels of expression of a gene or nucleotide sequence of interest.

As indicated, multiple copies of a UAR can be used to enhance the activity of the operably linked promoter. As noted, multiple copies of the same or different UARs can be utilized. For example, any combination of CaMV 35S UARs and maize Ubi-1 gene UARs can be utilized.

The promoters of this invention having one or more UARs as described above can be provided in expression cassettes and such cassetts contained in plasmid or viral vectors. Such vectors can be used for transformation of bacteria and plant cells. Transgenic plants can be ultimately regenerated from such transformed plant cells.

The UARs incorporated into plant promoters can substantially enhance transcription activity in transgenic plants. For example, one or more copies of the upstream activating region of the maize Ubi-1 gene can be operably linked to a promoter having the core synthetic promoter sequence and the synthetic upstream element of the invention. The promoter constructs of the invention can be operably linked to any nucleotide sequence or gene of interest. The promoter construct, for example, can be used to enhance oxalate oxidase gene expression in transgenic plants. Oxalate oxidase is a plant enzyme implicated in plant defense mechanisms against pathogens attack. The enzyme degrades the chemical compound oxalic acid secreted by plant pathogens. See e.g., PCT Publication No. WO 92/14824. Increasing the oxalate oxidase level in plants such as sunflower will lead to increased plant resistance to plant pathogens.

The following examples are for illustration purposes only and are intended in no way to limit the scope or application of the present invention. Those of skill in the art will appreciate that many permutations can be achieved and are in fact intended to be within the scope of the invention. All reference citations throughout the specification are expressly hereby incorporated by reference.

EXAMPLE 1

Plasmids were designed using the multiple cloning site of pBlueScriptIIKS+ from Stratagene. (To facilitate cloning of the different combination of elements). Oligonucleotides containing the sequences of the elements were synthesized with restriction endonuclease sites at the ends. Thus elements could be added or removed and replaced as needed. GUS and Luciferase were used for reporter genes.

For transient assays, plasmid DNA was introduced into intact 3-day-old maize seedlings by particle bombardment. Following 16 hours incubation at 25EC in the dark, expression was assayed by measuring GUS enzyme activity in root and shoot extracts from each seedling to determine if any tissue-preferred expression was demonstrated. GUS activity was measured using a GUS-Light assay kit from Tropix (47 Wiggins Avenue, Bedford, Mass. 01730).

Constructs that gave high levels of expression were introduced into a cell line to produce stable transformants. These stable transformants (TO) were assayed by PCR to determine the presence of the GUS gene by MUG (4-methylumelliferyl-glucuronide) assay to quantify the activity level of the GUS protein being produced. When the plants were ready to be transferred to the greenhouse they were assayed histochemically with X-gluc to determine where the GUS product was being synthesized. Plants demonstrating preferred expression levels were grown in the greenhouse to V6 stage.

EXAMPLE 2

Construction of Plasmids Containing the Syn II Core Promoter.

Standard molecular biological techniques were carried out according to Maniantis et al. (1982) Molecular Cloning: A Laboratory Manual, Cold Spring Harbor Laboratory, Cold Spring Harbor, N.Y. All plasmids utilized in the invention can be prepared according to the directions of the specification by a person of ordinary skill in the art without undue experimentation employing materials readily available in the art.

Figure 5:
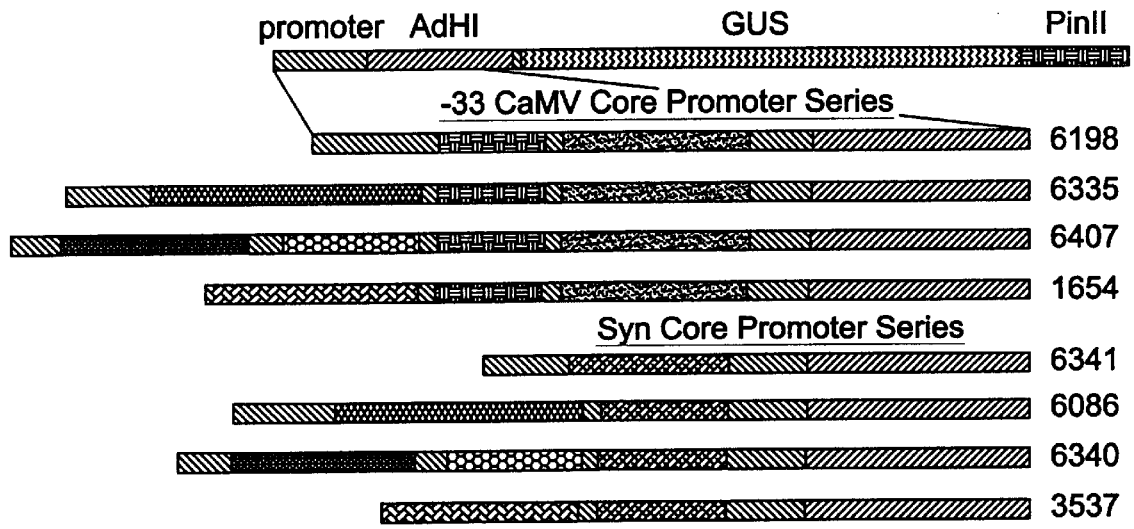
FIG. 5 depicts several schematics of synthetic promoters according to the present invention tested in transient and stable transformants.

Oligos N306 SEQ ID NO:6 5'-TCGACACTGC AGCTCTAGGG ATGGTAGCGC AGGGTGCGTA GGTACGTATT TATAGCCGCT CGAGTG-3' and N307 SEQ ID NO:7 5'-GATCCACTCG AGCGGCTATA AATACGTACC TACGCACCCT GCGCTACCAT CCTAGAGCT GCAGTG-3' were synthesized according to directions on an automated DNA synthesizer (such as Applied Biosystems Inc. DNA Synthesizer (Model 380B). These automated synthesizers are commercially available. The oligos were then ligated to the BamHI fragment of the pBlueScriptIIKS+ plasmid comprising of the β-glucuronidase gene interrupted by the maize ADH1 intron 1 region. A map of a plasmid incorporating both the Syn II Core promoter and the upstream element is disclosed as FIG. 4. Several other embodiments are shown in other plasmids depicted in FIG. 5. Plasmid numbers are shown to the right of each promoter diagram with the corresponding legend placed below the diagrams. The top diagram shows the complete transplant transcriptional unit with the subsequent diagrams focusing on the salient differences between 35S and Syn II Core promoters. The legend shows the number and nature of the various promoter subelements, the sequence if relatively short, the source of the element and position relative to the start of transcription.

Figure 6:
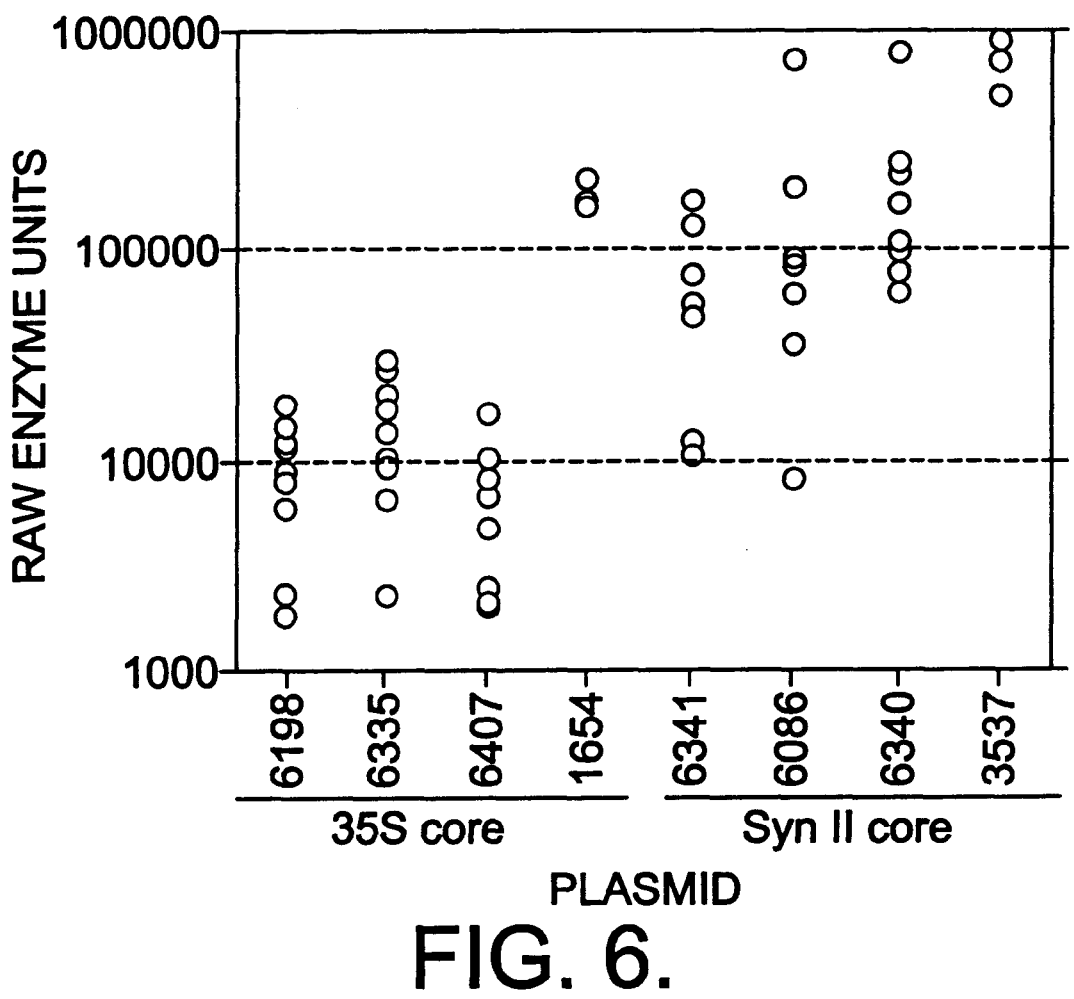
FIG. 6 is a depiction of transient assay data using the plasmids incorporating the promoter sequences of the invention.
Figure 7A:
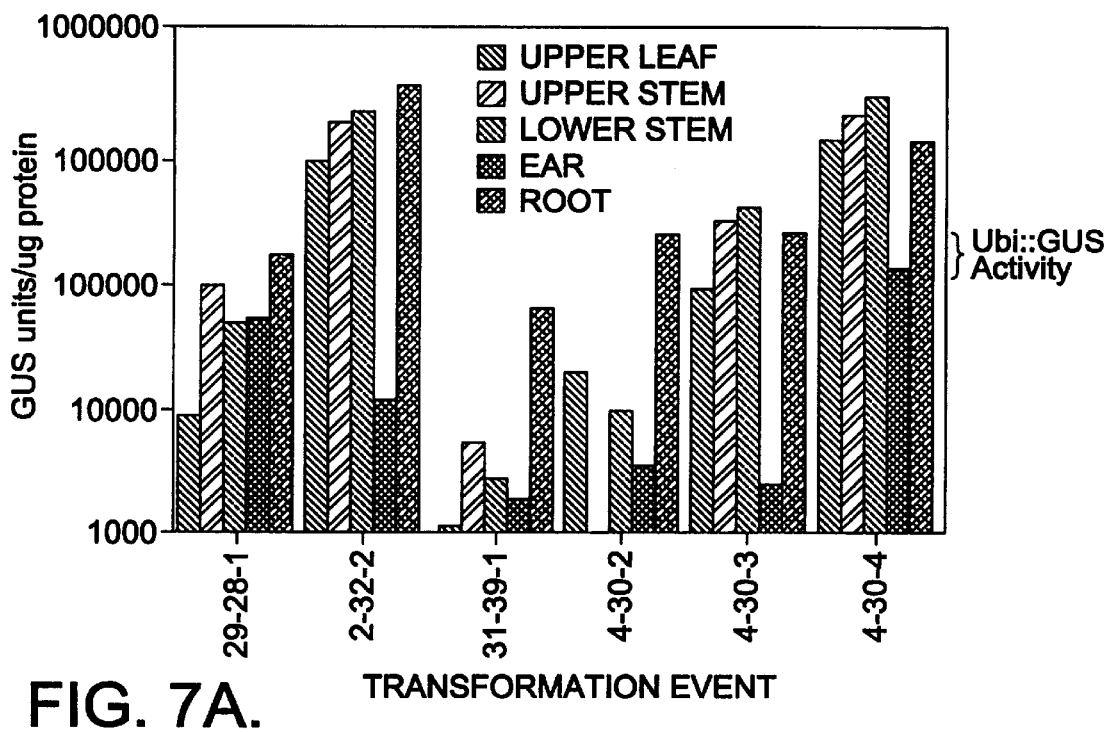
FIG. 7(A). Rsyn7::GUS (PHP6086) activity to T0 maize plants.
Figure 7B:
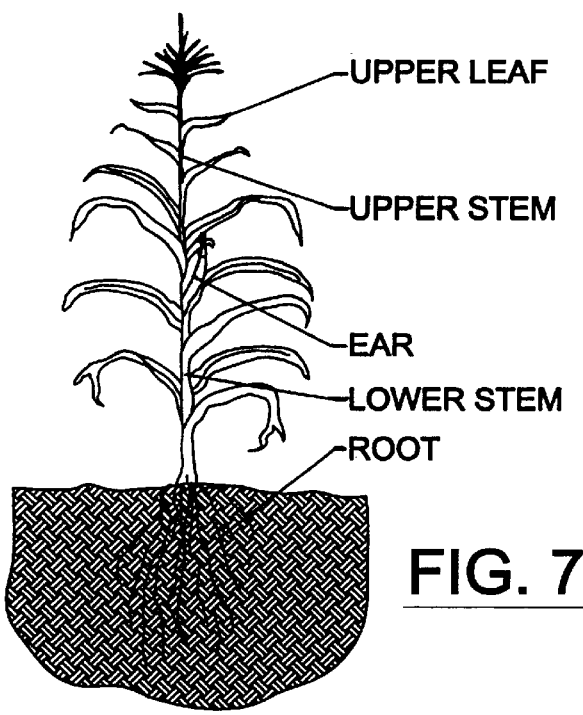
FIG. 7(B) is a schematic of VT stage corn plants with sites of tissue samples indicated.

The sequence of the core promoter consists of 35 base pairs with enzyme sites upstream of a TATA box and a start of transcription with 10 to 15 base pairs downstream. Upstream elements (Gal 4-binding sites, Rsyn, AT-GBL etc.) were fused to the core sequence with ADHI-intron and different marker genes (LUC or GUS) and were demonstrated functional both in transient assays (FIG. 6) and Rsyn stably transformed plants (FIG. 7).

EXAMPLE 3

Construction of Upstream Element Rsyn7 Fused to Syn II Core Promoter Resulting in Plasmids PHP5903 and PHP6086.

Oligos for constructing the Rsyn7 promoter subelement N1965: (SEQ ID NO:8) GATCCTATGA CGTATGGTAT GACGTGTGTT CAAGATGATG ACTTCAAACC TACCTATGAC GTATGGTATG ACGTGTGTCG ACTGATGACT TA-3' and N 1966: (SEQ ID NO:9) GATCTAAGTC ATCAGTCGAC ACACGTCATA CCATACGTCA TAGGTAGGTT TGAAGTCATC ATCTTGAACA CACGTCATAC CATACGTCA TAG-3' were synthesized as earlier described. The oligos were annealed and cloned into a PHP3398 plasmid upstream of the Syn II Core sequence and resulted in several versions of the original Rsyn7 sequence due to spontaneous deletions. The Rsyn7-2 version involved a single base deletion resulting in a 3× reiterative TGACG motif upstream of the Syn II Core promoter (Rsyn7::LUC, P5903). The LUC coding sequence was replaced by GUS coding sequence to produce the Rsyn7::GUS construct P6086. P6086 was later introduced into transgenic maize resulting in high levels of constitutive activity in four of the six active events examined (FIG. 7).

Figure 8:
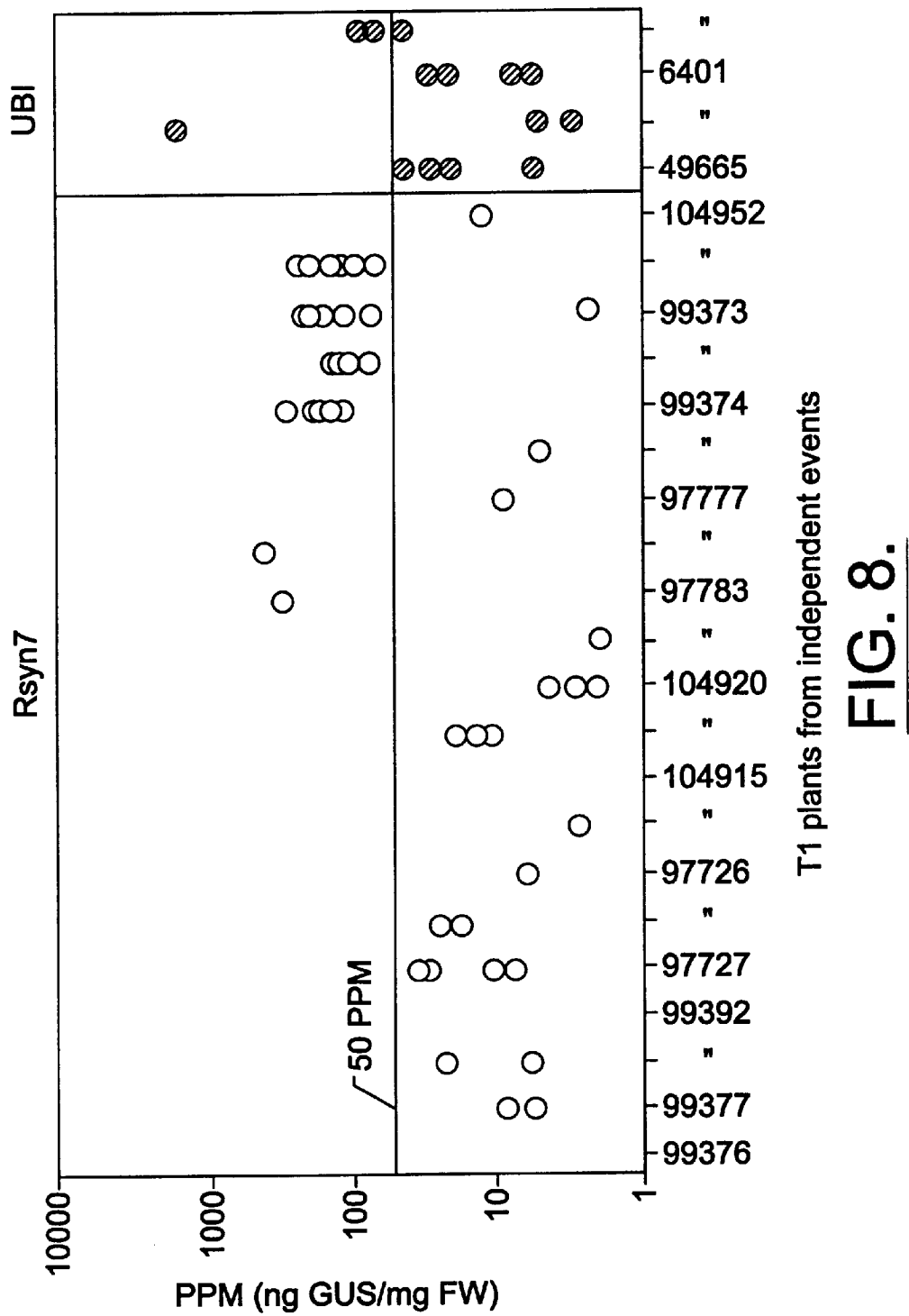
FIG. 8 depicts GUS activity in root segments of a segregating population of maize T1 transgenic seedlings containing the Rsyn7::GUS (PHP6086) or the UBI:GUS (PHP3953) construct.

The progeny from T0 plants from several transformation events were examined and GUS activity ranging from 1 to 400 PPM (micrograms GUS enzyme/GFW in root tissue of a 7-day old seedlings) FIG. 8. These T0 and T1 plants generally produced 4X–10 X greater GUS activity than plants harboring the ubiquitin::GUS reporter gene.

Thus from the foregoing, it can be seen that the invention accomplishes at least all of its objectives.

EXAMPLE 4
Transformation and Expression with Syn II Core Promoter and/or Rsyn7 Upstream Element.

Using transient bombardment assays the Syn II Core promoter sequence was compared against the 35S core sequence either alone or in conjunction with numerous activation elements. FIG. 6 is a depiction of transient assay data using the plasmids incorporating the promoter sequences of the invention and shows transient GUS or LUC activity in three-day old maize roots or BMS callus bombarded with chimeric promoter::GUS or LUC constructs. The −33 CaMV35S in the Syn II Core promoter versions of the synthetic promoter::GUS (or LUC) constructs were bombarded into three-day old roots (or cultured BMS calli as described hereinafter) and assayed for enzyme activity 20 hours after bombardments. The data shown are the raw enzyme units of a compilation of at least three experiments and have not been normalized in any fashion due to the inherent variability of the transient assays. Control plasmids 1654 and 3537 are the LUC constructs tested in maize BMS calli. There is approximately 4 to 20 fold difference in transient activity between the 35S and Syn II Core versions. The Y axis is in log scale. Both core promoters were driving a GUS containing construct (FIGS. 4 and 5) and generated a basal level of activity (FIG. 6). However when activator elements were placed upstream of the TATA motif, the Syn II Core provided generally higher levels of activity (2–4 fold better) in corn cells than when the activator elements were placed upstream of the 35S core (FIG. 6).

The Syn II Core sequence has been shown to enhance activity in stably transformed plants. Further with certain activator sequences upstream of the TATA element activity levels in stably transformed corn plants reached levels ten-fold greater than maize ubiquitin constructs which produces extremely high levels of activity.

FIGS. 7 and 8 show GUS activity levels from isolated tissues of VT stage T0 plants and root tissue from T1 seedlings, respectively. These data demonstrate that this core sequence can participate in potentiating very high levels of activity as a functional partner for the active chimeric promoters. FIG. 7 shows the Rsyn7::GUS (6086) activity in T0 maize plants. VT stage plants with ears post pollinated 3 to 8 days were dissected and assayed for GUS activity. 7A depicts GUS expression in designated tissues. 7B depicts a schematic of a corn plant with sites of measurement indicated. Plants from ro events that demonstrated a range of activities with the Rsyn7 promoter were assayed. Log scale again noted. The activity range for UBI::GUS plants is indicated at the right of graph for comparisons. These data demonstrate that the Rsyn7 promoter can increase activity to ten-fold above levels of the ubiquitin promoter yet shows little tissue preference making the Rsyn7 suitable as a strong constitutive promoter.

FIG. 8 depicts GUS activity in root segments of a segregating population of maize T1 transgenic seedlings containing the Rsyn7::GUS (6086) or the UBI::GUS (3953) construct. 1 cm root segments from six to seven-day old transgenic maize seedlings were dissected, weighed and assayed for GUS using GUS-light kit. Activity is represented as parts per million of fresh weight. The root activity of several T1 plants harboring the Rsyn7::GUS promoter shows higher activity than much of the activity levels produced by the UBI promoter. This is consistent with data from T0 transgenic plant. Activity levels in Rsyn7::GUS containing young leaves are also much higher than the activity levels of UBI::GUS-containing young leaves (data not shown). The Syn II Core sequence was shown to function well with a variety of upstream elements including GAL 4 binding sites, Rsyn7 elements, GBL elements, etc.

Figure 9:
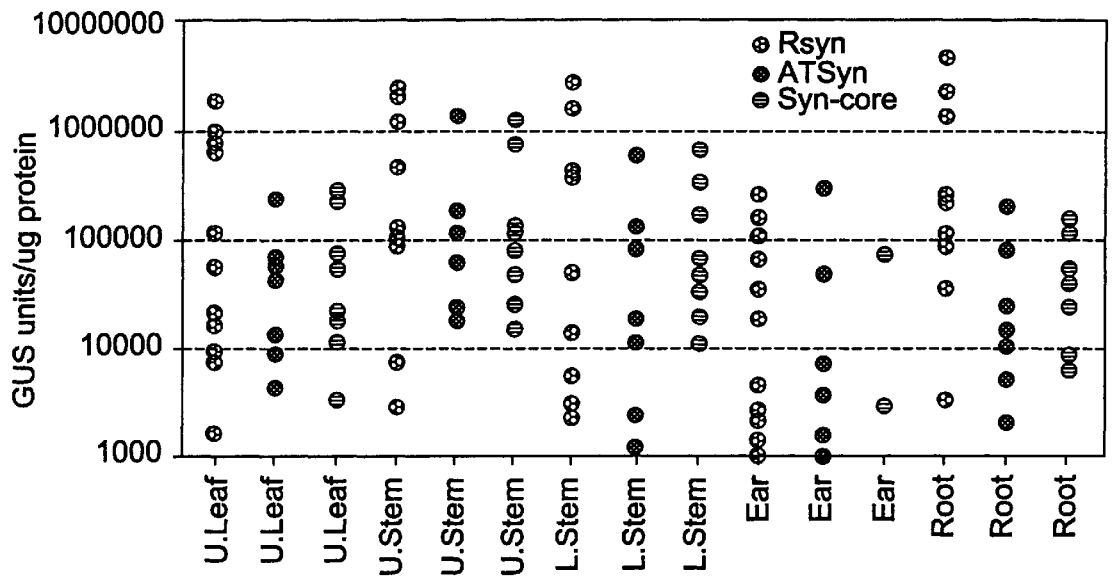
FIG. 9 depicts GUS expression of three synthetic promoters in T0 transgenic maize plants including the promoter sequences of the invention as comparison.
Figure 9:
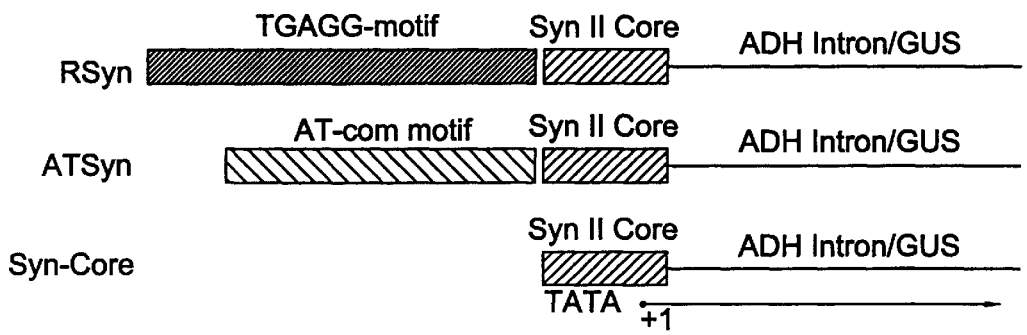

FIG. 9 shows GUS expression of three synthetic promoters in T0 transgenic maize plants. Dissected tissues (See FIG. 7B) from VT stage transgenic T0 plants harboring Rsyn7 (Rsyn), Atsyn or the Syn II Core alone (syn-core) promoter::GUS constructs were quantitatively assayed for GUS activity. Each circle represents an average of tissue activity of transgenic maize plants from a single transformation event. The TGACG-motif corresponds to the Rsyn7 sequence and the "AT-com" motif refers to the consensus AT-like composite element, Atcom, from W. Gurley, et al. 1993. In: Control of Plant Gene Expression. ed. by Desh Pal Verma. CRC press, Boca Raton, Fla. pp. 103–123. Syn-core refers to the Syn II Core promoter sequence containing the TATA element and the start of transcription.

EXAMPLE 5
Construction of Rsyn7 Promoter Having the Upstream Activating Regions from the CaMV 35S Gene and the Maize Ubi-1 Gene.

To construct an expression vector having 35SU (upstream activating regions from 35S gene)-Rsyn7 promoter, PHP413 was digested with BglII and EcoRV. The staggered/sticky ends of the linearized vector were filled in by Klenow in the presence of dNTP. The 2× CaMV fragment was blunt end ligated into BamH1 digested PHP6086 after filling the BamHI ends. The CaMV 35S-Rsyn7 fragment was then cut out from the new construct by digestion with Xba1 and Pst 1, and ligated into the 4 kb XbaI-Pst1 vector from PHP9925 to form the expression vector of 35SU-Rsyn7::GUS (PHP9778).

To construct an expression vector having UbiU (upstream activating elements from the maize Ubi-1 gene)-Rsyn7 promoter, the Xba1-Spe1 fragment from PHP8277 was ligated into the Xba1 site of PHP6086 to form PHP10539, into the Xba1 site of PHP10970 to form PHP10971, and into the Xba1 site of PHP10971 to form the expression vector of Ubi-1-Rsyn7::GUS (PHP 10972).

Those sequences not referenced otherwise include:

SEQ ID NO: 11 sets forth the 35S UAR.

SEQ ID NO: 12 sets forth the SCPI promoter sequence, (35S UAR operably linked to core promoter of SEQ ID NO: 1).

SEQ ID NO: 13 sets forth the Ubi1 UAR.

SEQ ID NO: 14 sets forth SCP1 operably linked to the oxalate oxidase coding sequence operably linked with the PinII terminator.

SEQ ID NO: 16 sets forth the UCP2 promoter sequence (2 copies of Ubi1 UAR operably with the core promoter).

SEQ ID NO: 18 set forth the UCP4 promoter sequence (4 copies of Ubi1 UAR operably with the core promoter).

EXAMPLE 6
Transformation and Expression of promoter constructs.

The various promoters::GUS fragments were cloned into a Bin9 binary vector that contains ALS3::NPTII as selection marker for generating transgenic sunflower callus or Arabidopsis.

For transient expression, SMF3 sunflower seeds were planted in greenhouse. 15-day-old seeds after pollination were collected from the plants and used in the transient expression system. After removing the pericarp, the cotyledons with seed coats were sterilized by incubation in 20% bleach at RT for 15 minutes, and washed four times with sterile double distilled water. The cotyledons were then incubated on 3MM filter wetted with MS medium overnight before they were bombarded according to the method disclosed by Klein et al. (1989) Proc. Natl. Acad Sci. USA 86:6681–6685, hereby incorporated by reference thereto. GUS activity was analyzed 20 hours after bombardment using the GUS-Light assay kit from Tropix according to the manufacturer's protocol.

For leaf disc transformation, young expanded SMF3 sunflower leaf from 30-day-old sunflower was harvested and sterilized in 20% bleach with a couple of drops of Tween 20 for 20 minutes. Leaf discs were prepared from the sterile leaves after washing them with sterile double distilled water 4 times. The leaf discs were then incubated for 10 minutes in inoculation medium (12.5 mM MES, 1 g/l $NH_4Cl$, and 0.3 g/l $MgSO_4$) containing Agrobacterium (EHA105) transformed with the vector constructs to be tested at A600=0.75. The leaf discs were then grown for 3 days in non-selection medium and were then transferred to selection medium.

To transform Arabidopsis, Arabidopsis were grown in greenhouse to the stage when bolts start to emerge at 15 plants/pot. The emerging bolts were clipped off to encourage the growth of multiple secondary bolts. After 7 days, the plants were ready for infiltration. Agrobacterium (EHA105) carrying the construct to be tested was cultured at 28 °C. to when A600 was between 0.65 and 0.8. The cells were harvested in inoculation medium (4.3 g/l of MS salt, 0.5 mg/l of nicotinic acid, 0.5 mg/l of pyridoxine-HCl, 1 mg/l of Thiamine-HCl, 0.1 g of myo-inositol, 1 g/l of casamino acids, 0.01 mg of BAP, 68.5 g/l of sucrose, and 36 g/l of glucose) at A600 of 7.5.

The clipped plants to be transformed were inverted into a 250 ml beaker containing the above Agrobacterium solution. The beaker was placed into a bell jar and was vacuumed until bubbles formed on leaf and stem surface. After 15 minutes of infiltration, the vacuum was released and the plants were removed from the beaker, laid on its side in a plastic flat, and covered with plastic wrap. The plants were set upright and grown in greenhouse for four weeks before seeds were harvested. Transgenic seeds were selected by planting the seeds on a medium plate containing 65 µg/ml of kanamycin.

Figure 10:
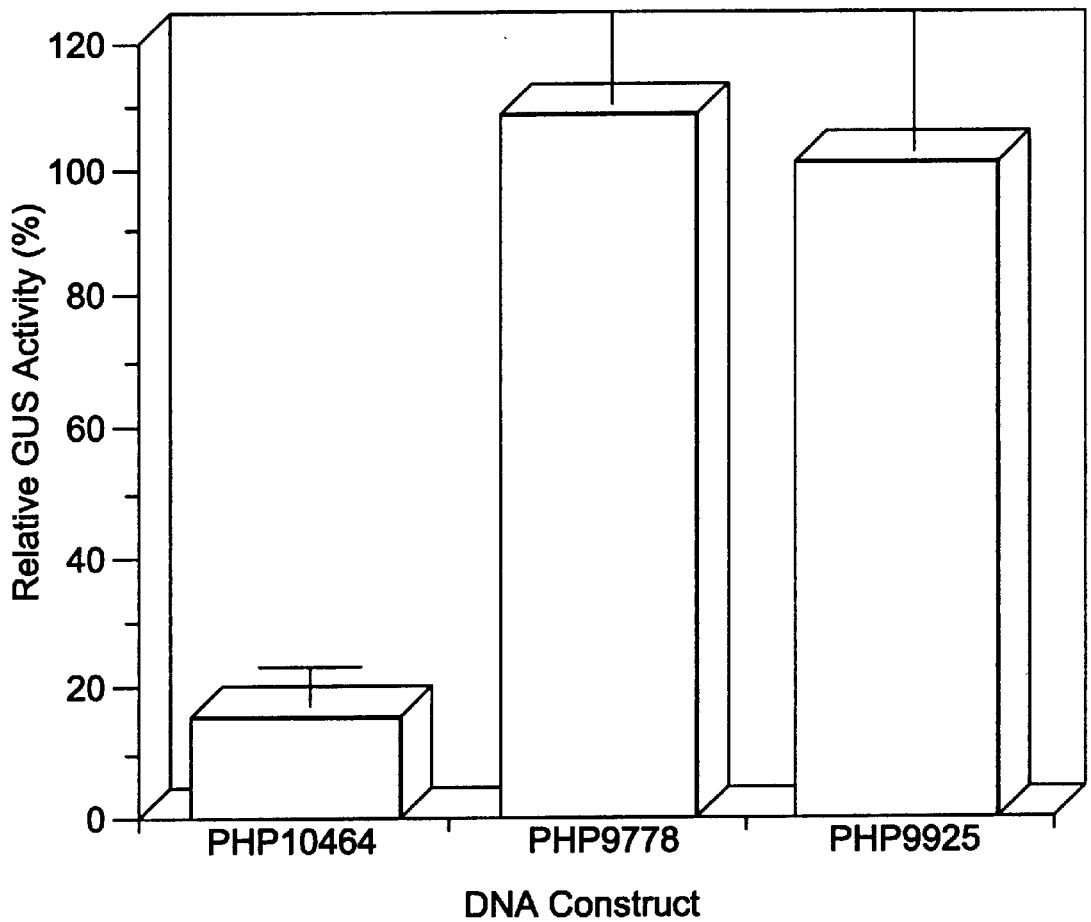
FIG. 10 shows the comparison of the activities of the Rsyn7 promoter, the CaMV 35S promoter, and the 35SU-Rsyn7 promoter in transient expression in sunflower cotyledons.

In transient expression assays, the Rsyn7 promoter in PHP10464 has 15% of the 35S promoter (PHP9925) activity, whereas the 35SU-Rsyn7 promoter (PHP9778) (hereinafter SCP1 promoter) has about 107% of the 35S promoter activity (FIG. 10). Thus, the upstream activating region of the CaMV 35S gene increased the Rsyn7 activity by about 6 fold.

Figure 11:
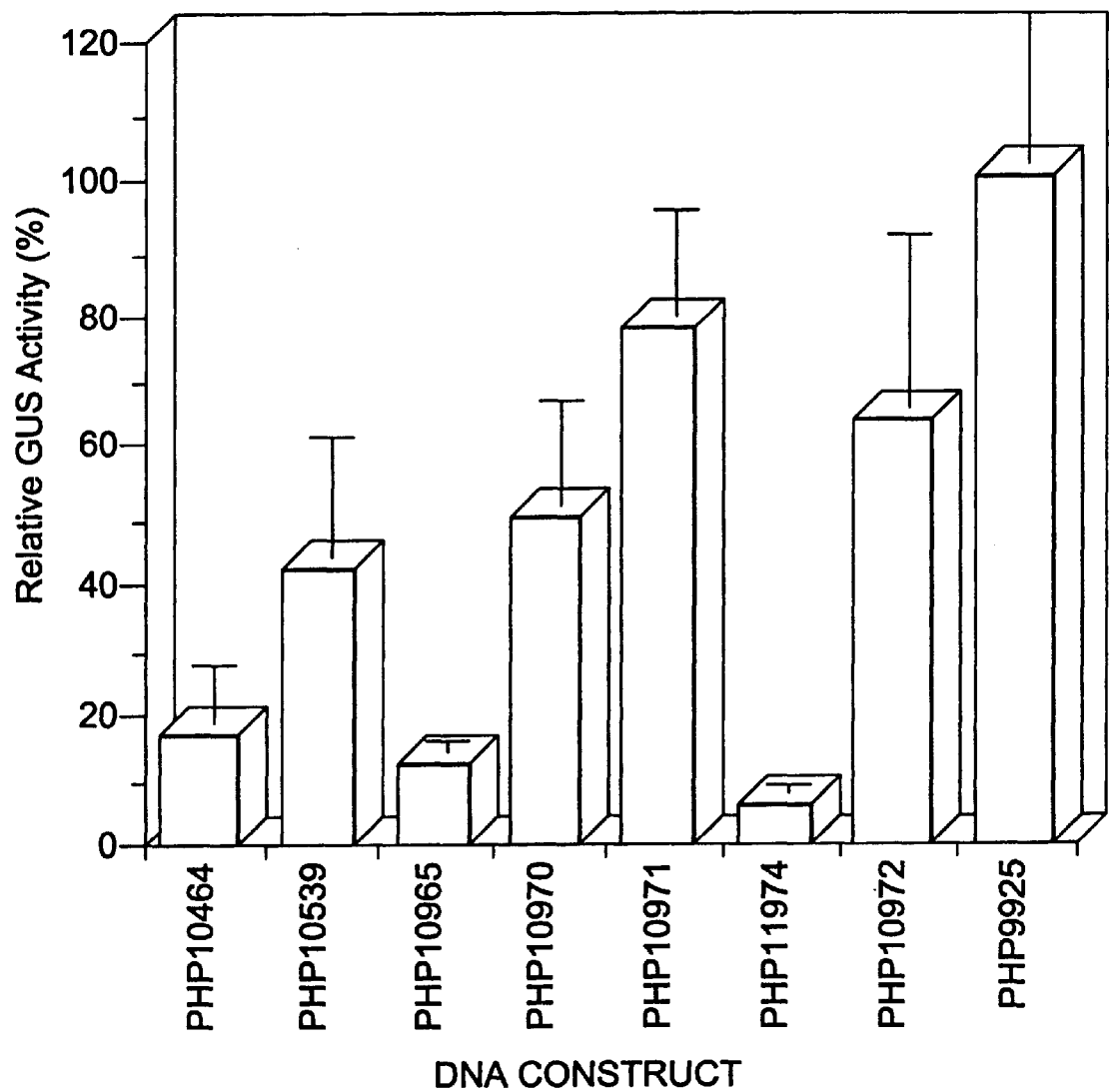
FIG. 11 shows the effect of the Ubi-1 upstream activating region on the strength of the Rsyn 7 promoter in transient expression in sunflower cotyledons.

The maize Ubi-1 upstream element (UbiU) has similar effects on the Rsyn7 promoter in transient assays. When the upstream activating region (UAR) of the maize Ubi-1 was fused to Rsyn7, the GUS enzyme activity increased with the number of copy of the UAR. In the presence of three copies of the UbiU, GUS activity increased by about 4-fold. This additive effect of UbiU was not observed when placed in the context of the maize ubiquitin promoter (PHP 11974). This suggests that replacement of the maize Ubi1 core promoter with Rsyn7 may convert the monocot Ubi1 promoter into a highly active promoter in dicot plants (FIG. 11).

Figure 12:
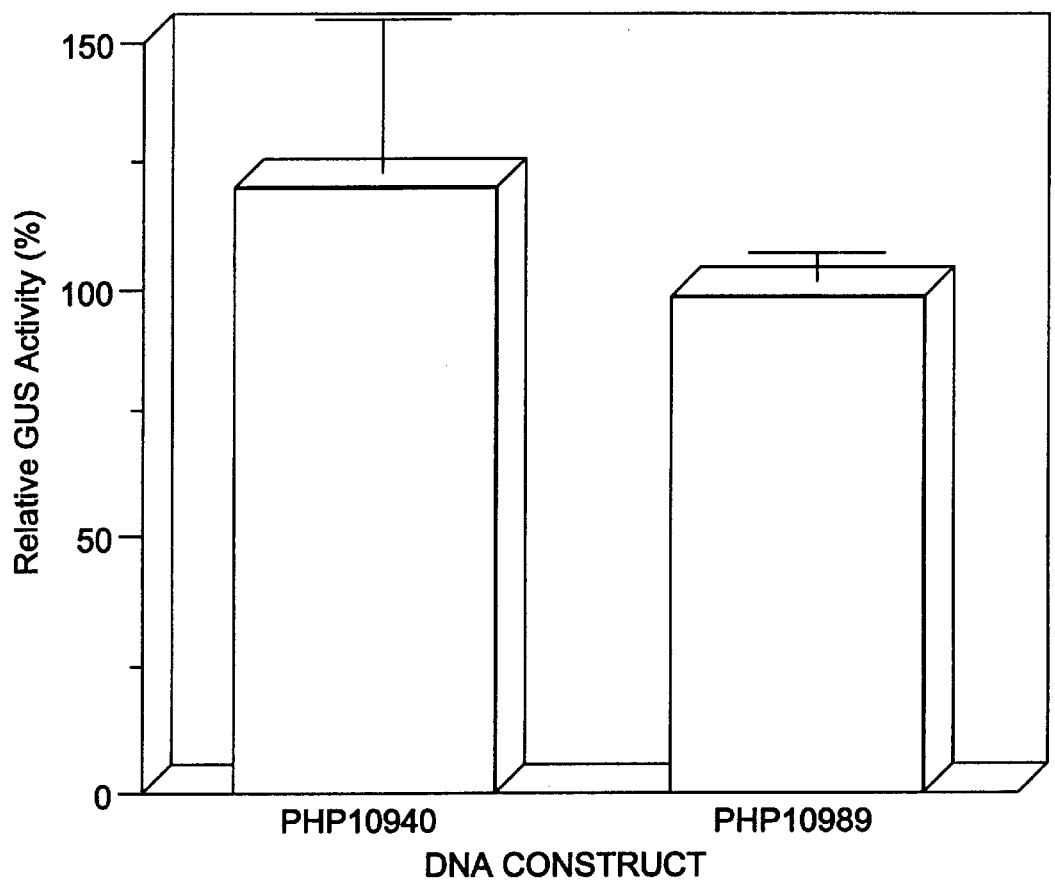
FIG. 12 shows that in the stably transformed sunflower callus, GUS expression behind the control of the 35SU-Rsyn7 is 20% higher than when behind the control of the 35S CaMV promoter.

In the stably transformed sunflower callus, GUS expression is 20% higher behind the control of the 35SU-Rsyn7 (SCP1 promoter) promoter than when behind the control of the 35S CaMV promoter(FIG. 12).

Figure 13:
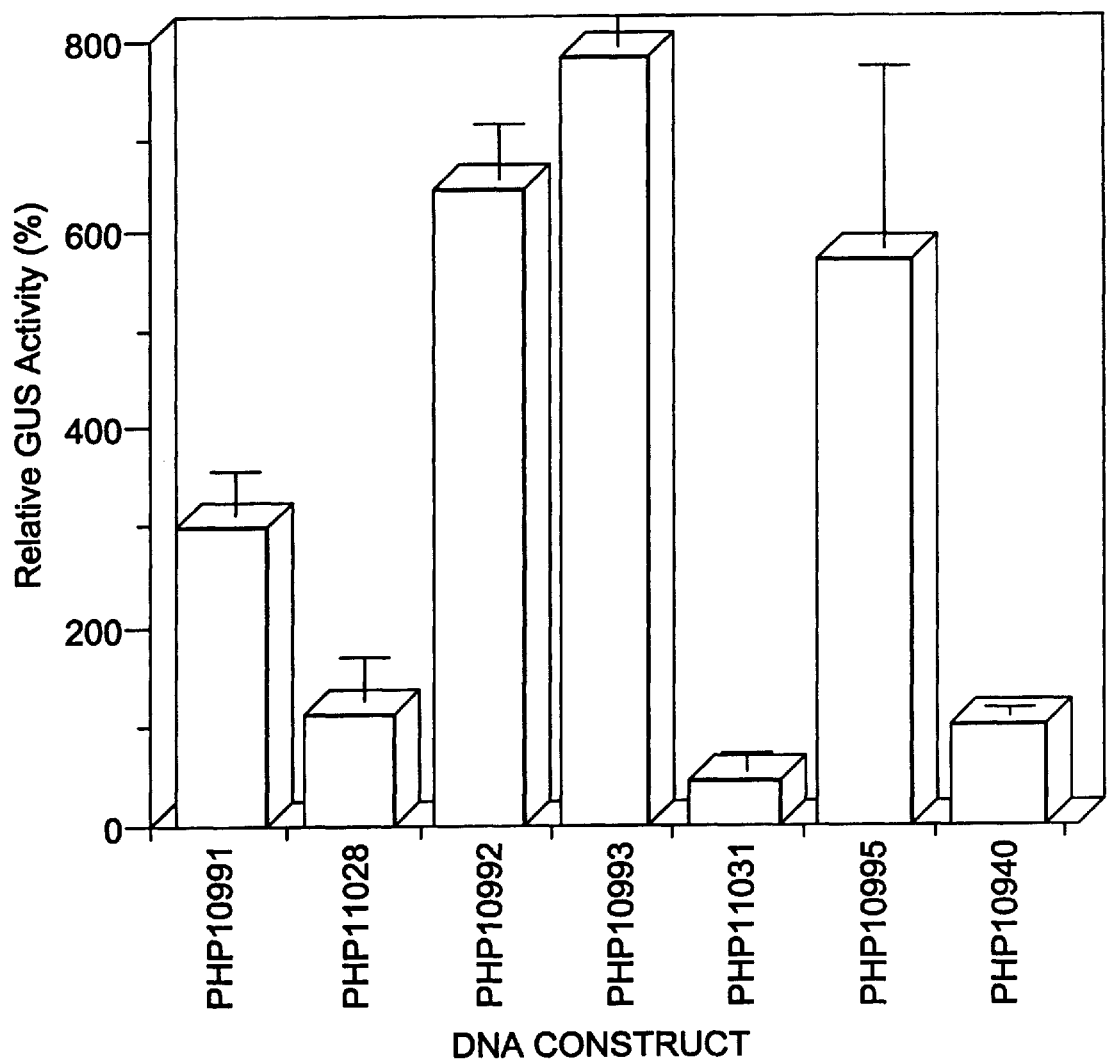
FIG. 13 shows the effect of the Ubi-1 upstream activating region on the activity of the Rsyn7 promoter in transgenic sunflower callus assay.

The results of the transgenic callus assay are given in FIG. 13. The Rsyn7 promoter containing a single copy of UbiU (PHP10991) (hereinafter UCP1 promoter) (SEQ ID NO:15) exhibited promoter activity of about 3 times that of the 35SU-Rsyn7 (SCP1) promoter (PHP 10940). Three copies of UbiU (PHP 10993) increased Rsyn7 promoter activity to about 7 times that of the 35SU-Rsyn7 promoter. The 3×UbiU-Rsyn7 (UCP3 promoter) (SEQ ID NO: 17) is by far the strongest promoter in sunflower tissues.

To determine the activity and tissue-specificity of the enhanced Rsyn7 promoters, stably-transformed sunflower and Arabidopsis were generated through Agrobacterium-mediated transformation. The histochemical staining of GUS expression in transgenic T1 Arabidopsis indicates that 35SU-Rsyn7 (SCP1 promoter) (PHP10940) has identical tissue-specificity and similar activity as 35S CaMV promoter (PHP10989). Both promoters express GUS in leaf stem, petiole, and floral parts. UbiU-Rsyn7 (USCP1 promoter) (PHP10991) exhibits higher activity than maize Ubi-1 promoter (PHP 11031) in Arabidopsis stem and leaf tissues.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A synthetic DNA promoter sequence functional in a plant cell, said promoter sequence comprising a TATA motif, a transcription start site, and a region between said TATA motif and said start site that is at least 64% GC-rich; wherein said region is not a region between a TATA motif and a transcription start site of native maize ubiquitin promoter, and wherein said promoter sequence is set forth in SEQ ID NO:10.

2. A synthetic DNA promoter sequence functional in a plant cell, said promoter sequence comprising a TATA motif, a transcription start site, and a region between said TATA motif and said start site that is at least 64% GC-rich; wherein said region is not a region between a TATA motif and a transcription start site of native maize ubiquitin promoter, and wherein said promoter sequence is set forth in SEQ ID NO:1.

3. An expression cassette comprising a synthetic promoter comprising a TATA motif, a transcription start site and a region between said TATA motif and said start site that is at least 64% GC rich, a structural gene operatively linked to said promoter, and a transcription end site polyadenylation signal; wherein said region is not a region between a TATA motif and a transcription start site of native maize ubiquitin promoter, and wherein sequence of said promoter is set forth in SEQ ID NO:1.

4. An expression cassette comprising a synthetic promoter comprising a TATA motif, a transcription start site and a region between said TATA motif and said start site that is at least 64% GC rich, a structural gene operatively linked to said promoter, and a transcription end site polyadenylation signal; wherein said region is not a region between a TATA motif and a transcription start site of native maize ubiquitin promoter, and wherein sequence of said promoter is set forth in SEQ ID NO:10.

5. An expression cassette comprising a synthetic promoter comprising a TATA motif, a transcription start site and a region between said TATA motif and said start site that is at least 64% GC rich, a structural gene operatively linked to said promoter, a transcription end site polyadenylation signal, and an upstream element operatively linked to said promoter so that transcription is enhanced; wherein said region is not a region between a TATA motif and a transcription start site of native maize ubiquitin promoter; and wherein sequence of said upstream element is set forth in SEQ ID NO:2.

6. A nucleic acid vector comprising the promoter of any of claims 2 or 3 operatively linked to a structural gene and an upstream element operatively linked to said promoter, wherein sequence of said upstream element is set forth in SEQ ID NO:2.

7. A synthetic upstream element having a sequence set forth in SEQ ID NO:2.

8. An expression cassette comprising:

a promoter sequence;

a structural gene operatively linked to said promoter sequence;

a polyadenylation signal; and a synthetic upstream element comprising SEQ ID NO:2 operatively linked to said promoter so that expression is enhanced.

9. The expression cassette of claim 8, wherein said synthetic promoter sequence is SEQ ID NO:2.

10. A nucleic acid vector comprising the expression cassette of claim 8.

11. The vector of claim 10, wherein said synthetic upstream element is SEQ ID NO:2.

12. A prokaryotic or eukaryotic host cell transformed with the vector of claim 10.

13. An isolated nucleotide sequence comprising a DNA enhancer sequence comprising the nucleotide sequence set forth in SEQ ID No: 5.

14. A nucleotide sequence comprising a promoter construct, said construct comprising in operable linkage a core promoter sequence and a Ubi-1 UAR, wherein said Ubi-1 UAR is a maize Ubi UAR comprising the sequence set forth in SEQ ID No: 13.

15. An expression cassette comprising in operable linkage a core promoter sequence, a Ubi UAR operably linked upstream to said core promoter to form a synthetic promoter construct, a nucleotide sequence of interest operably linked to said synthetic promoter, and a polyadenylation signal; wherein said Ubi-1 UAR comprises the sequence set forth in SEQ ID No:13.

* * * * *